(12) United States Patent
Chiosis et al.

(10) Patent No.: US 7,439,359 B2
(45) Date of Patent: Oct. 21, 2008

(54) SMALL MOLECULE COMPOSITIONS FOR BINDING TO HSP90

(75) Inventors: Gabriela Chiosis, New York, NY (US); Neal Rosen, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/415,868

(22) PCT Filed: Nov. 1, 2001

(86) PCT No.: PCT/US01/46303

§ 371 (c)(1), (2), (4) Date: May 1, 2003

(87) PCT Pub. No.: WO02/36075

PCT Pub. Date: May 10, 2002

(65) Prior Publication Data

US 2004/0102458 A1    May 27, 2004

Related U.S. Application Data

(60) Provisional application No. 60/245,177, filed on Nov. 2, 2000.

(51) Int. Cl.
*C07D 473/40* (2006.01)
*C07D 473/30* (2006.01)
*C07D 473/34* (2006.01)
*A61K 31/52* (2006.01)
*A61K 31/522* (2006.01)
*A61P 35/00* (2006.01)

(52) U.S. Cl. ............. 544/277; 544/264; 544/265; 544/276

(58) Field of Classification Search ............. 544/264, 544/265, 267, 271, 272, 273, 276, 277; 514/263.3, 514/263.34, 263.37, 263.38, 263.4
See application file for complete search history.

(56) References Cited

U.S. PATENT DOCUMENTS

| | | | | |
|---|---|---|---|---|
| 2,729,642 | A * | 1/1956 | Burgison | 544/272 |
| 3,930,005 | A * | 12/1975 | Wojnar et al. | 514/263.37 |
| 4,172,829 | A * | 10/1979 | Naito et al. | 514/263.37 |
| 5,110,818 | A * | 5/1992 | Allgeier | 514/263.4 |
| 5,387,584 | A | 2/1995 | Schnur | |
| 5,565,566 | A * | 10/1996 | Olsson | 544/277 |
| 5,714,494 | A * | 2/1998 | Connell et al. | 514/263.23 |
| 5,736,549 | A * | 4/1998 | Beasley et al. | 514/263.23 |
| 5,932,566 | A | 8/1999 | Schnur et al. | |
| 6,210,974 | B1 | 4/2001 | Gold | |
| 6,294,541 | B1 * | 9/2001 | Cavalla et al. | 514/263.22 |
| 6,335,157 | B1 | 1/2002 | Gonzalez et al. | |
| 6,413,975 | B1 | 7/2002 | Chasin et al. | |
| 6,440,982 | B1 | 8/2002 | Maw et al. | |
| 6,946,456 | B2 * | 9/2005 | Rosen et al. | 514/183 |
| 2005/0049263 | A1 * | 3/2005 | Kasibhatla et al. | 514/263.21 |
| 2005/0113340 | A1 * | 5/2005 | Kasibhatla et al. | 514/81 |
| 2007/0129334 | A1 * | 6/2007 | Kasibhatla et al. | 514/81 |

FOREIGN PATENT DOCUMENTS

| | | |
|---|---|---|
| EP | 193454 A1 * | 9/1986 |
| WO | WO 96/32480 | 10/1996 |
| WO | WO 96/40789 | 12/1996 |
| WO | WO 97/04801 | 2/1997 |
| WO | WO 98/51702 | 11/1998 |
| WO | WO 00/59449 | 10/2000 |
| WO | WO 00/61578 | 10/2000 |

OTHER PUBLICATIONS

Obermann, J Cell Biol. Nov. 16, 1998;143(4):901-10.*
Panouse, Annales Pharma. Francaises 58(5) 291-302 (Oct. 2000; Conference presentation Jan. 19, 2000).*
17-AAG <http://www.geldanamycin.com/17aag.htm> downloaded from the Internet Sep. 7, 2005.*
Stebbins Cell, vol. 89, 239-250, 1997.*
Lucas et al., Journal of Combinatorial Chemistry (2001), 3(6), 518-520 (Web Release Date: Sep. 21, 2001).*
Basso et al., Akt forms and intracellular complex wih heat shock protein 90 (Hsp90) and cdc37 and is destabilized by inhibitors of . . . , The Journal of Biological Chemistry, Oct. 18, 2002, pp. 39858-39866, vol. 277, No. 42, Publisher: The American Society for Biochemistry and Molecular Biology, Inc.

Bharadwaj et al., Multiple components of the HSP90 chaperone complex function in regulation of heat shock factor 1 in vivo, Molecular and Cellular Biology, 1999, pp. 8033-8041, vol. 19, No. 12, Publisher: American Society for Microbiology.

Chene, ATPases as drug targets: learning from their structure, Nature Reviews, 2002, pp. 665-673, Publisher: Nature Publishing Group.

Chiosis et al., A small molecule designed to bind to the adenine nucleotide pocket of Hsp90 causes Her2 degradation and the growth . . . , Chemistry & Biology, 2001, pp. 289-299, Publisher: Elsevier Science Ltd.

Jez et al., Crystal structure and molecular modeling of 17-DMAG in complex with human hsp90, Chemistry & Biology, 2003, pp. 361-368, vol. 10, Publisher: Elsevier Science Ltd.

Maloney et al., HSP90 as a new therapeutic target for cancer therapy: the story unfolds, 2002, pp. 3-24, Publisher: Ashley Publications, Published in.

Roe et al., Structural basis for inhibition of the hsp90 molecular chaperone by the antibiotics radicicol and geldanamycin, J. Med. Chem, 1999, pp. 260-266, vol. 42, Publisher: American Chemical Society.

Rui et al., Chemistry and pharmacology of new potent analgesic epibatidine, 1999, pp. 313-326, vol. 11, No. 3, Published in: Shanghai, China.

Schulte et al., Disruption of the Raf-1-Hsp90 molecular complex results in destabilization of Raf-1 and loss of Raf-1-Ras association, The Journal of Biological Chemistry, Oct. 13, 1995, pp. 24585-24588, vol. 270, No. 41.

Schulte et al., Antibiotic radicicol binds to the N-terminal domain of hsp90 and shares important biologic activities with geldanamycin, Cell Stress & Chaperones, 1998, pp. 100-108, Publisher: Harcourt Brace and Co Ltd.

Stebbins et al., Crystal Structure of an Hsp90-Geldanamycin Comples: Targeting of a Protein Chaperone by an Antitumor Agent, Molecular Biology, Apr. 18, 1997, pp. 239-250, vol. 89.

Xu et al., Sensitivity of mature ErbB2 to geldanamycin is conferred by its kinase domian and is mediated by the chaperone protein , The Journal of Biological Chemistry, Feb. 2, 2001, pp. 3702-3708, vol. 276, No. 5.

Zou et al., Repression of heat shock transcription factor HSF1 activation by HSP90 (HSP90 Complex) that forms a stress-sensitive . . . , Cell, Aug. 21, 1998, pp. 471-480, vol. 94, Publisher: Cell Press.

Black et al. "Reaction of Ninhydrin With Activated Anilines: Formation of Indole Derivatives." Ietrahdron. 1994, vol. 50, No. 37, pp. 10983-10994. See Compound 17.

Kato et al. "Synthesis of Compounds Related to Antitumor Agents IV. On The Reaction of Aromatic Carboxylates With 2,4 Diamino-5-hydroxy-6-methylpyrimidine." Chem. Pharm. Bull. 1076, vol. 24, No. 10, pp. 2461-2469. See Table 2.

Chavany, et al. "p185erbB2 Binds to GRP94 in Vivo", Journal of Biological Chemistry, vol. 271, No. 9 Mar. 1, 1996, pp. 4974-4977.

Neckers, "Effects of Geldanamycin and Other Naturally Occurring Small Molecule Antagonists of Heat Shock Protein 90 on HER2 Protein Expression", Breast Disease 11 (2000) 49-59. pp. 49-59.

Schnur, et al. "erbB-2 Oncogene Inhibition by Geldanamycin Derivatives: Synthesis, Mechanism of Action, and Structure—Activity Relationships", J. Med. Chem. 1995, 38, 3813-3820.

Stockwell, et al. High-throughput screening of small molecules in miniaturized mammalian cell-based assays involving post-translational modifications, Chemistry & Biology, Feb. 1999, 6:71-83.

* cited by examiner

*Primary Examiner*—Mark L Berch
(74) *Attorney, Agent, or Firm*—Marina Larson & Associates, LLC

(57) ABSTRACT

Structural differences in binding pockets of members of the HSP90 family can be exploited to achieve differential degradation of kinases and other signaling proteins through the use of designed small molecules which interact with the N-terminal binding pocket with an affinity which is greater than ADP and different from the ansamycin antibiotics for at least one species of the HSP90 family. Moreover, these small molecules can be designed to be soluble in aqueous media, thus providing a further advantage over the use of ansamycin antibiotics. Pharmaceutical compositions can be formulated containing a pharmaceutically acceptable carrier and a molecule that includes a binding moiety which binds to the N-terminal pocket of at least one member of the HSP90 family of proteins. Such binding moieties were found to have antiproliferative activity against tumor cells which are dependent on proteins requiring chaperones of the HSP90 family for their function. Different chemical species have different activity, however, allowing the selection of, for example Her2 degradation without degradation of Raf kinase. Thus, the binding moieties possess an inherent targeting capacity. In addition, the small molecules can be linked to targeting moieties to provide targeting of the activity to specific classes of cells. Thus, the invention further provides a method for treatment of diseases, including cancers, by administration of these compositions. Dimeric forms of the binding moieties may also be employed.

7 Claims, 22 Drawing Sheets

```
 21  * AFQAEIAQLM SLIINTFYSN KEITLRELIS NSSDALDKIR
 81  $ EVNRMM KLINSLYKN KEITLRELIS NASDALDKIR LISL
 21  # AQLM SLIINTFYSN KEITLRELIS NASDALDKIR YESLT
 91  @ QAETKKLLDIVARSLYSE KEVFIRELIS NASDALEKIR HK

61  * YETLTDPSKL DSGKELHINL IPNKQDRTLT IVDTGIGMTK ADLINNLGTI AKSGTKAFME
121  $ TDENALSGNE ELTVKIKCDK EKNLLHVTDTGVGMTR EELVKNLGTI AKSGTSEFLNKMTE
 61  # DPSKLDSGKE LKIDIIPNPQ ERTLT LVDTGIGMIK ADLINNLGTI AKSGTKAFME
131  @ LVSDGQALPE MEIHLQTNAE KGITIQDTGIGMTQ EELVSNLGTI ARSGSKAFLDALQNQ

121  * ALQAGADISM    IGQFGVGFYS AYLVAEKVTV ITKHNDDEQ YAWESSAGGSF TVRTDTGEPM
181  $ AQEDGQSTSEL   IGQFGVGFYS A ELVADKVIV TSKHNNDTQ HIWESDSNEF SVIADPRGNT
116  # ALQAGADI SM   IGQFGVGFYS AYLVAEKYYV IRKHNDDEQ YAWESS AGGSFIVRAD HGEPIGM
186  @ ALQNQABASSKI IGQFGVGFYS AFMVADRVEYYSR SAAPGSLGYQ WLSDGSGVFE

181  * GRGTKVILH LKEDQTEYLEE RRIKHIVKKH SQFIGYPITL FVEKERDKEV SDDEAEKED
241  $ LGRGTIITLV LKEEASDYLE LDTTKENLVKK YSQFINRPIY VWSSKTETVE EPMEEEEAAK
176  # GMGTKVILH LKEDQTEYLEE RRVKEVVKKHSQFIG
246  @ GVRIGTKII IH LKS DCKEFSSEARV RDVVTKYSNF

* HSP90 ALPHA (P07900); $ GRP94 (NP_003290); # HSP90 BETA (P08238); @ TRAP1 (AAF15314)
```

Fig 1

Reagents: (a) HF, pyridine, t-butyl nitrite; (b) R₁OH, PPh₃, diethyl azodicarboxylate or di-tert-butyl azodicarboxylate, toluene:DCM.(c) R₂OH, NaOMe; (d) CH₂I₂, isoamyl nitrite; (e) Bu₃SnCN, Pd[PPh₃]₄; (f) (MeCN)₂PdCl₂, Bu₃(vinyl)Sn.

Synthesis of class II small molecules. Variations of X2.
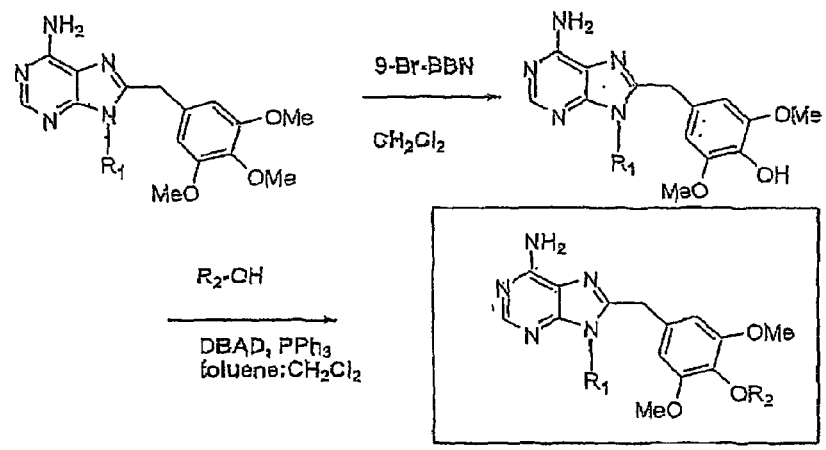
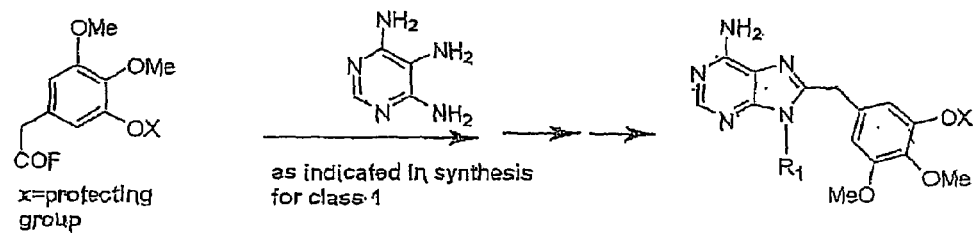
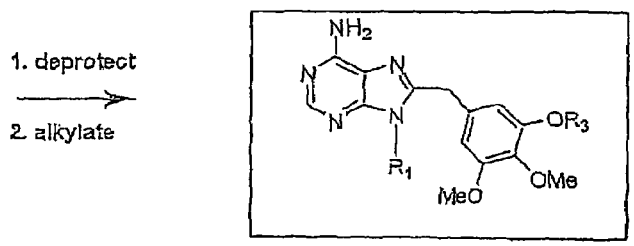
R2 and R3 any
Fig 8A

Reagents: (a) HX, *t*-butylhydroperoxide.

Reagents: (a) 3,4,5-trimethoxyaniline; (b) 3,4,5-trimethoxyphenol; (c) 3,4,5-trimethoxybenzyl alcohol Mode of attachment of PU3 (as example molecule of PU family) to other entities(another PU3=dimer, an inhibitor or a carrier molecule=antibody etc)
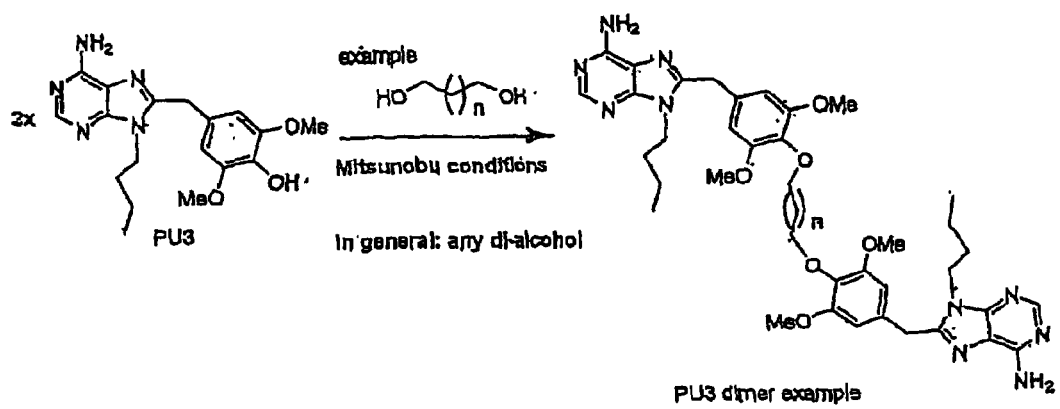
PU3 dimer example
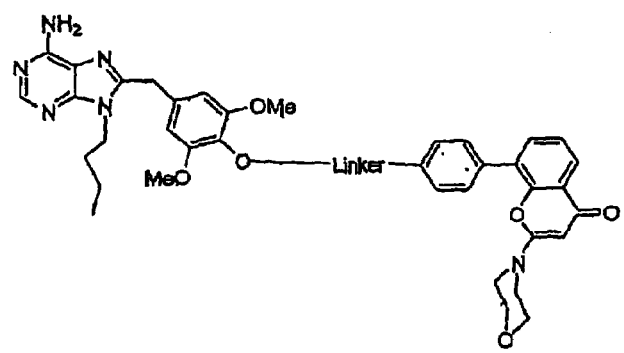
General example of PU3 heterodimer:
PU3 linked to the PI3K inhibitor, LY294002
Fig 11

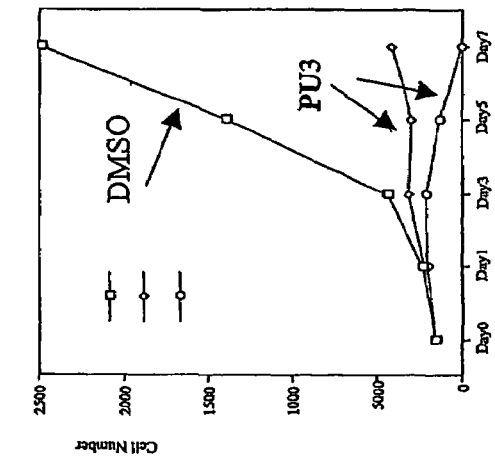
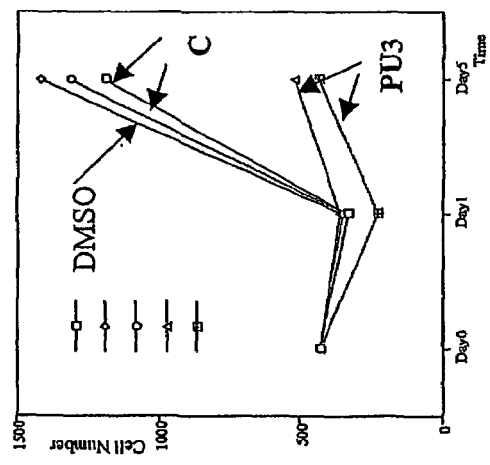
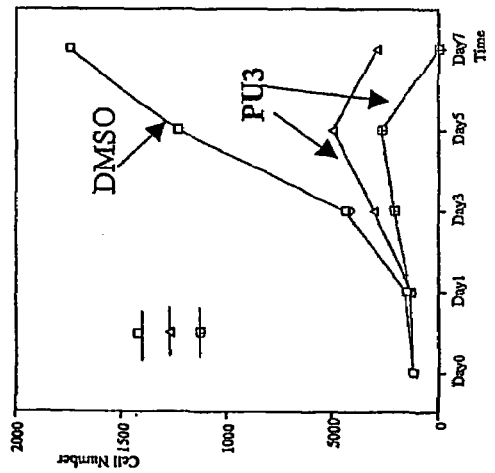
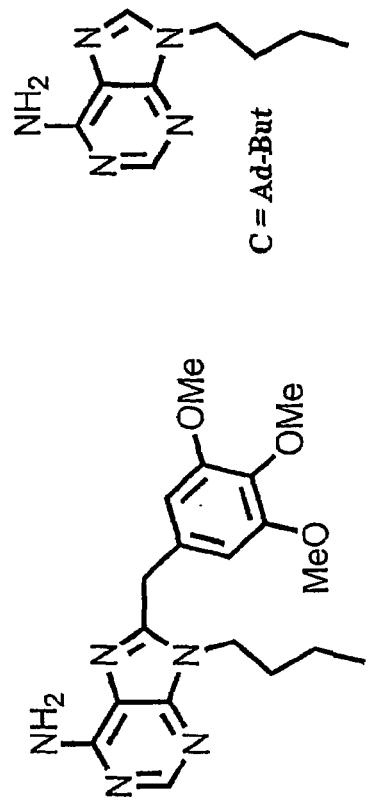
Fig. 14A
Fig. 14B
Fig. 14C

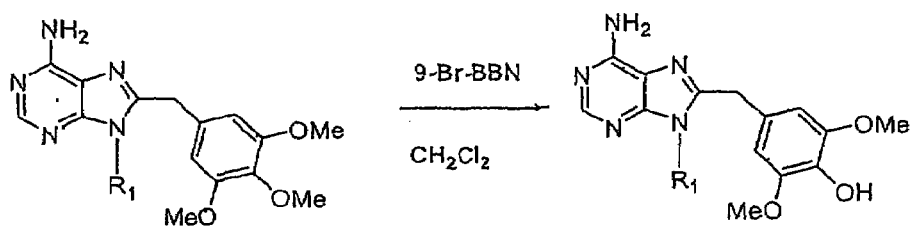

Charge 50mg of PU3 to 4mL anhydrous CH2Cl2. Charge 2mL of 1M 9-BrBBN in CH2Cl2 (15equivalents). Stir for 1hr at room temperature. Add 4mL NaHCO3. Stir 15min. Split and extract aqueous with 3x5mL CH2Cl2. Concentrate. Column on silica gel with 10:5:5:1.5=hexanes:CH2Cl2:EtOAc:MeOH. 25mg product=52% yield.

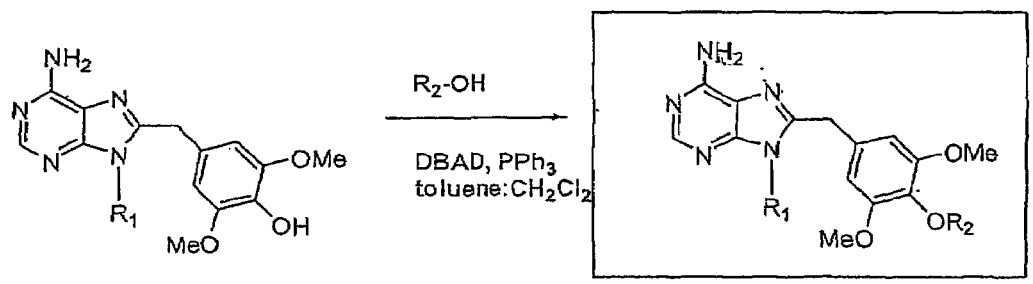

R₁ is (CH3)2CHCH2-

5mg of SM (0.014mmol), 8mg PPh3 (2eq), 16mg di-*t*-butylazodicarboxylate (5equivalents), 2μL ROH (1.5eq) in 0.4mL CH2Cl2 were added till all dissolved. Add 1.3mL toluene. Stir at RT 16hrs..Concentrate Column silica gel with 10:5:5:1.5=hexanes:CH2Cl2:EtOAc:MeOH.

| ROH | yield% |
|---|---|
| ⟩─OH | 17 |
| MeO⁀⟶OH | 43 |
| ⟩N⁀⟶OH | 35 |

Fig 16A

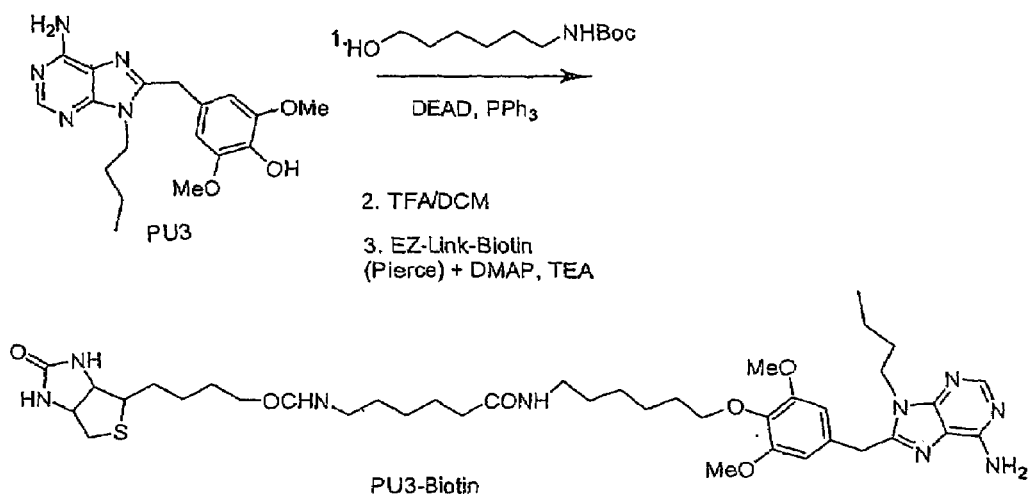

Exp. To Sepharose-Streptavidin [40uL/exp] were added increasing concentrations of PU3-Biotin and the slurry equilibrated for 15min at rt. Beads were washed with PBS 0.2%Tween and 30uL of RSBT buffer were added to each sample, followed by identical amounts of proteins [Hsp90 or Trap]. Samples were rocked for 1hr at 4°C. After several washes the amount of bound protein was eluted by boiling in 50uL 1xSDS buffer. Proteins were assessed by immunoblotting.

SMALL MOLECULE COMPOSITIONS FOR BINDING TO HSP90

This application claims the benefit of U.S. Provisional Application No. 60/245,177, filed Nov. 2, 2000, which is incorporated herein by reference.

BACKGROUND OF THE INVENTION

This application relates to small molecules that bind to the HSP90 family of proteins, and to methods for making and using such small molecules.

The HSP90 family of proteins has four recognized members in mammalian cells: Hsp90 α and β, Grp94 and Trap-1. Hsp90 α and β exist in the cytosol and the nucleus in association with a number of other proteins. Hsp90 is the most abundant cellular chaperone, and has been shown in experimental systems to be required for ATP-dependent refolding of denatured or "unfolded"proteins. It has therefore been proposed to function as part of the cellular defense against stress. When cells are exposed to heat or other environmental stresses, the aggregation of unfolded proteins is prevented by pathways that catalyze their refolding or degradation. This process depends on the association of the unfolded protein in an ordered fashion with multiple chaperones (Hsp 60, 90 and 70 and p23), forming a "refoldosome" and ultimately the ATP-dependent release of the chaperones from the refolded protein.

Hsp90 may also play a role in maintaining the stability and function of mutated proteins. It seems to be required for expression of mutated p53 and v-src to a much greater extent than for their wild-type counterparts. It has been suggested that this occurs as a result of hsp90-mediated suppression of the phenotypes of mutations that lead to protein unfolding.

Hsp90 is also necessary to the conformational maturation of several key proteins involved in the growth response of the cell to extracellular factors. These include the steroid receptors as well as certain transmembrane kinases (i.e., Raf serine linase, v-src and Her2). The mechanism whereby hsp90 affects these proteins is not fully understood, but appears to be similar to its role in protein refolding. In the case of the progesterone receptor, it has been shown that binding and release of hsp90 from the receptor occurs in a cyclic fashion in concert with release of other chaperones and immunophilins and is required for high affinity binding of the steroid to the receptor. Thus, hsp90 could function as a physiologic regulator of signaling pathways, even in the absence of stress.

Hsp90 has also been shown to be overexpressed in multiple tumor types and as a function of oncogenic transformation. Whether it plays a necessary role in maintaining transformation is unknown, but it could have at least three functions in this regard. Cancer cells grow in an environment of hypoxia, low pH and low nutrient concentration. They also rapidly adapt to or are selected to become resistant to radiation and cytotoxic chemotherapeutic agents. Thus, the general role of hsp90 in maintaining the stability of proteins under stress may be necessary for cell viability under these conditions. Secondly, cancer cells harbor mutated oncogenic proteins. Some of these are gain-of-function mutations which are necessary for the transformed phenotype. Hsp90 may be required for maintaining the folded, functionally-active conformation of these proteins. Thirdly, activation of signaling pathways mediated by steroid receptors, Raf and other hsp90 targets is necessary for the growth and survival of many tumors which thus probably also require functional hsp90.

These characteristics of hsp90 make it a viable target for therapeutic agents. HSP90 family members possess a unique pocket in their N-terminal region that is specific to and conserved among all hsp90s from bacteria to mammals, but which is not present in other molecular chaperones. The endogenous ligand for this pocket is not known, but it binds ATP and ADP with low affinity and has weak ATPase activity. In addition, the ansamycin antibiotics geldanamycin (GM) and herbimycin (HA) have been shown to bind to this conserved pocket. This binding affinity has been shown for all members of the HSP90 family. International Patent Publication No. WO98/51702, which is incorporated herein by reference, discloses the use of ansamycin antibiotics coupled to a targeting moiety to provide targeted delivery of the ansamycin leading to the degradation of proteins in and death of the targeted cells. International Patent Publication No. WO00/61578 relates to bifunctional molecules having two moieties which interact with the chaperone protein hsp90, including in particular homo- and heterodimers of ansamycin antibiotics. These bifunctional molecules act to promote degradation and/or inhibition of HER-family tyrosine kinases and are effective for treatment of cancers which overexpress Her-kinases.

While the use of geldanamycin and other ansamycin antibiotics and their derivatives provides for effective degradation of a number of kinases and other signaling proteins, they generally lack significant selectivity, and are instead effective to degrade a broad spectrum of proteins. This can increase the risk of undesirable side effects. Furthermore, anasmycin antibiotics are insoluble or at best poorly soluble in aqueous media. This complicates administration. Thus, there remains room for improvement of therapeutic agents that bring about the degradation of kinases and other signaling proteins via interaction with members of the HSP90 family of chaperone proteins.

SUMMARY OF THE INVENTION

While the members of the HSP90 family of proteins are characterized by a unique N-terminal binding pocket that is highly conserved, there are structural differences between the pockets of the various members. It has now been found that these structural differences can be exploited to achieve differential degradation of kinases and other signaling proteins through the use of designed small molecules which interact with the N-terminal binding pocket with an affinity which is greater than ADP and different from the ansamycin antibiotics. Moreover, these small molecules can be designed to be soluble in aqueous media, thus providing a further advantage over the use of ansamycin antibiotics.

The N-terminal pockets of the HSP90 of family of proteins contain five potential binding sites. In the case of hsp90 α, these binding sites are:

(a) a top binding site comprising Lys112,
(b) a second top binding site comprising Lys58, Asp54, Phe138 backbone, Gly 135 and Asn106;
(c) a bottom binding site comprising Asp93, Ser52 and Asn51;
(d) a hydrophobic lateral binding site comprising Val150, Met98, Val186, Phe138, Leu107, Leu103, Val186 and Trp162; and
(e) a small hydrophobic bottom binding site comprising Thr184, Val186, Val150 and Ile91.

The present invention provides pharmaceutical compositions comprising a pharmaceutically acceptable carrier and a molecule comprising a binding moiety which binds to the N-terminal pocket of at least one member of the HSP90 family of proteins. This binding moiety interacts with the N-terminal pocket with an affinity greater than ADP but less than geldanamycin for at least one specifies protein in the HSP90 family. Further, the binding moiety has a backbone which can achieve a folded C-configuration when disposed within the N-terminal pocket of a member of the HSP90 family of proteins. The binding moiety also has substituents on the backbone directed in orientations to interact with a plurality of the potential binding sites within the N-terminal pocket.

The binding moieties of the invention were found to have antiproliferative activity against tumor cells which are dependent on proteins requiring chaperones of the HSP90 family for their function. Different chemical species have different activity, however, allowing the selection of, for example Her2 degradation without degradation of Raf kinase. Thus, the binding moieties of the invention possess an inherent targeting capacity. In addition, the small molecules can be linked to targeting moieties to provide targeting of the activity to specific classes of cells. Thus, the invention further provides a method for treatment of diseases, including cancers, by administration of these compositions. Dimeric forms of the binding moieties may also be employed.

BRIEF DESCRIPTION OF THE DRAWINGS

FIG. 1 shows aligned sequences of amino acids contributing to the N-terminal binding pocket in known members of the HSP90 family of chaperone proteins, Hsp90 α (Seq. ID No. 1), GRP94 (Seq. ID. No. 2), Hsp90 β (Seq. ID No. 3) and Trap1 (Seq. ID. No. 4);

FIG. 11 shows dimerization or the addition of targeting moieties;

FIGS. 14A-C show the antiproliferative effect of PU3 on breast cancer cell lines;

FIGS. 16A and B show a procedure for modifying PU3 and using biotinylation for immobilization;

DETAILED DESCRIPTION OF THE INVENTION

The present invention relates to small molecules which bind preferentially and with an affinity greater than ADP and less than geldanamycin to the N-terminal pocket of one or more members of the HSP90 family of proteins, for example, to one or more of hsp90 α or β, Grp94 and Trap-1, or proteins with similar pockets, for example DNA gyrase and MutL. As used in the specification and claims of this application, the term "N-terminal pocket of HSP90" refers to the pocket to which geldanamycin and other ansamycin antibiotics bind, and which is occupied by ATP/ADP.

FIG. 1 shows aligned sequences comparing the structures of each of the known members of the HSP90 family of proteins. In the case of hsp90 α, the five potential binding sites are:

(a) a top binding site comprising Lys112;
(b) a second top binding site comprising Lys58, Asp54, Phe138 backbone, Gly 135 and Asn106;
(c) a bottom binding site comprising Asp93, Ser52 and Asn51;
(d) a hydrophobic lateral binding site comprising Val150, Met98, Val186, Phe138, Leu107, Leu103, Val186 and Trp162; and
(e) a small hydrophobic bottom binding site comprising Thr184, Val186, Val150 and Ile91.

As indicated in FIG. 1, the N-terminal pocket, while highly conserved in HSP90 family of proteins, does have differences between the various members. The binding moieties of the invention exploit these differences to provide compositions which afford differential degradation of kinases and other signaling proteins. As used in the specification and claims of this application, the term "differential degradation" refers to either degradation of one kinase or signaling protein to a greater extent than another kinase or signaling protein, where both would be degraded in the presence of geldanamycin, or to the degradation of a kinase or signaling protein to a different product than would be obtained in the presence of geldanamycin.

The size and shape of the N-terminal binding pocket are described in Stebbins et al., "Crystal Structure of an Hsp90-Geldanamycin Complex: Targeting of a Protein Chaperone by an Antitumor Agent" *Cell* 89: 239-250 (1997). There it is observed that "the pocket can be described as a flat-bottomed cone; it is about 15 Å deep, 12 Å in diameter near its surface, 8 Å midway down, and wide enough at the bottom to hold three water molecules. The binding moieties in the pharmaceutical compositions of the invention are designed to fit within this pocket, and to interact with a plurality of the potential binding sites within the N-terminal pocket.

Figure 2:
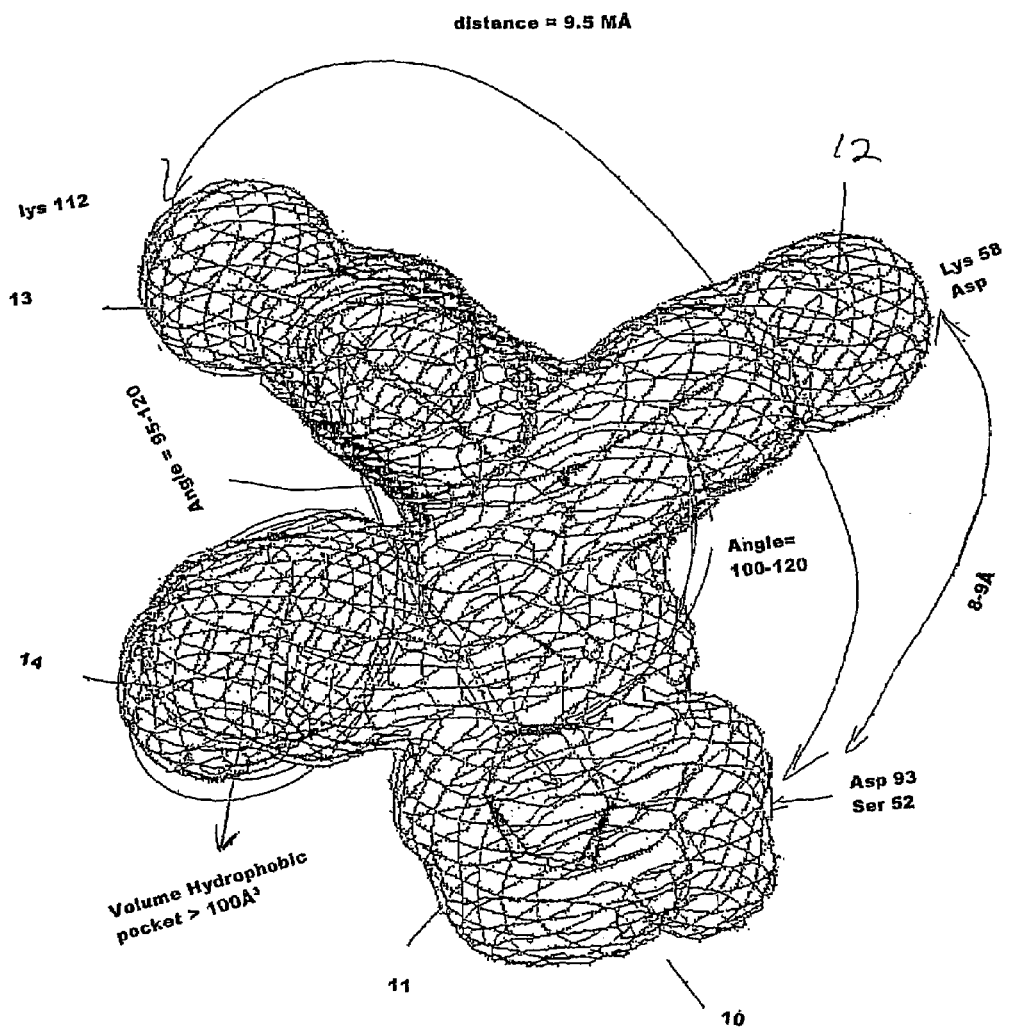
FIG. 2 shows a three dimensional drawings of the pocket with a binding moiety of the invention disposed therein.
Figure 3B:
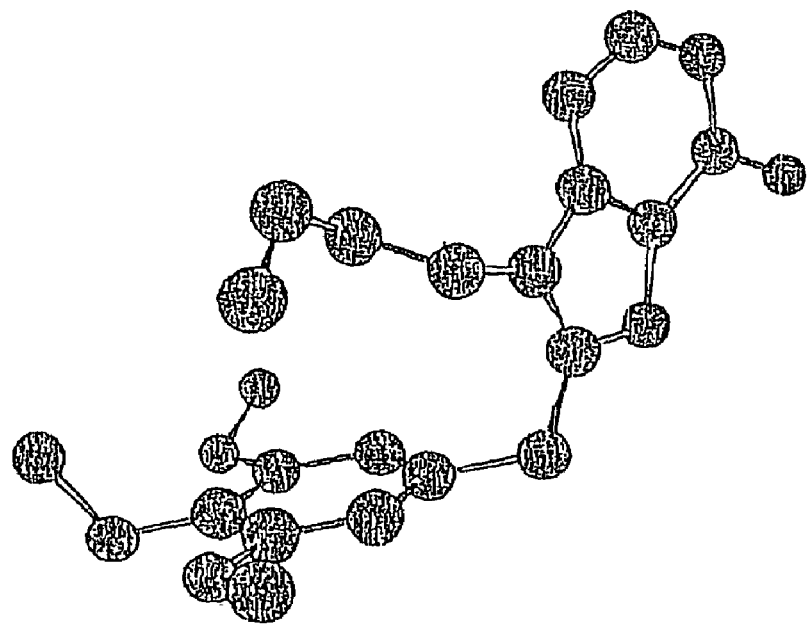
FIGS. 3A and B show the conformation of PU3 inside the hsp90 pocket, as determined by molecular modeling, and outside of the pocket as determined by x-ray crystallography.
Figure 3A:
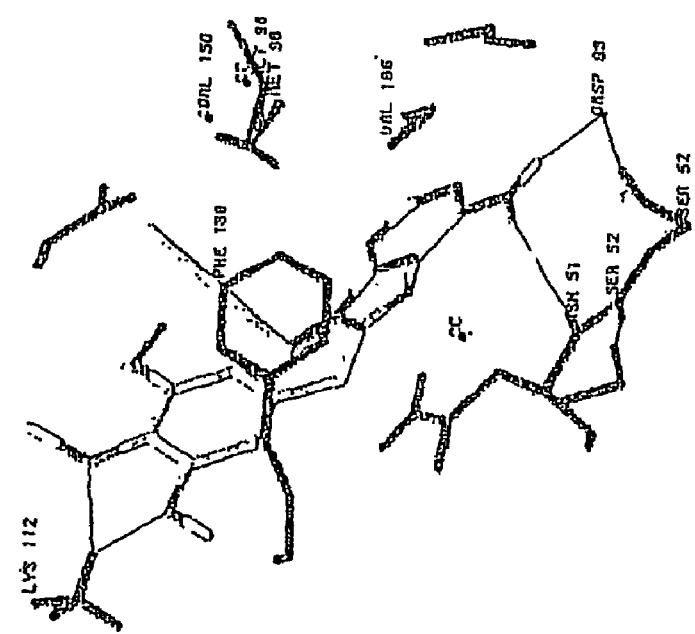
Figure 4:
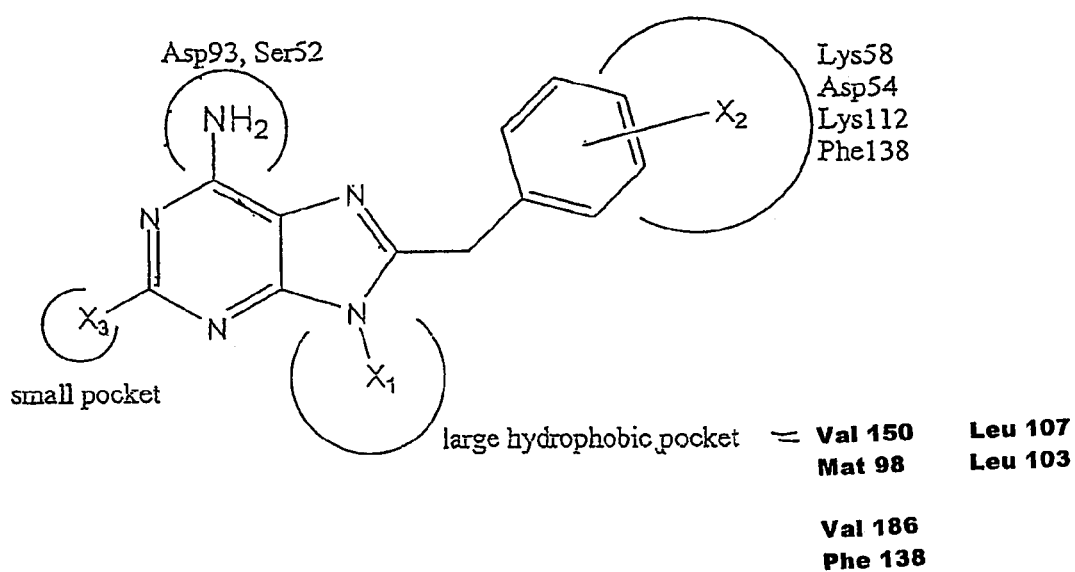
FIG. 4 shows an exemplary binding moiety/compound based on a purine nucleus, and indicates the interactions of the various substituents with binding sites in the N-terminal pocket of members of the HSP90 family.

FIG. 2 shows a three dimensional drawing of the pocket with a binding moiety of the type shown in FIG. 4 disposed therein to assist in visualizing the molecular design process. FIGS. 3A and B show the conformation of a designed binding moiety based on a purine nucleus (PU3) inside the hsp90 pocket, as determined by x-ray crystallography, inside the pocket, and without the pocket shown, respectively. The opening 10 of the pocket is disposed near the bottom of the figure. The pocket itself has four arms, arm 11 which is nearest the opening 10 and which include the bottom binding site. As reflected in the FIG. 4, the interior of this arm interacts with the amino substituent of the purine nucleus.

Second arm 13 connects to the first arm at an angle of about 95-110° C. Third arm 12 connects to the first arm 11 at an angle of about 100-120°. These two arms contain the two binding sites and are generally hydrophilic in nature. The substituent $X_2$ (FIG. 4) fits within one of these two arms, resulting in the bending of the binding moiety into the characteristic C-shape. The ability to adopt this C-shape must be taken into account when selecting molecules to act as binding moieties. As noted in FIG. 2, the separation between arms 11 and 13 (9.5 to 11 Å) is greater than the separation between arms 11 and 12 (8-9 Å). Thus, selection of a longer substituent ($X_2$) may favor insertion of the molecule into arm 13 over arm 12. The fourth arm 14 contains the lateral hydrophobic pocket, and receives the substituent $X_1$ (FIG. 4). This pocket has a volume of ≈100 Å$^3$ and is generally hydrophobic in character. Thus, the substituent $X_1$ (FIG. 4) is selected to fill this pocket and to interact with the hydrophobic residues.

In a first embodiment of the invention, the binding moiety is a complete molecule. FIG. 4 shows an exemplary structure of this type based on a purine nucleus, and indicates the interactions between the substituents and the binding sites within the N-terminal binding pocket. In FIG. 4, the substituent $X_1$ may be any hydrophobic chain (linear, branched aliphatic, aromatic, acyclic or cyclic, containing C, H, N, O and/or S atoms that fits within the pocket); $X_2$ is from 1 to five hydrogen acceptor functionalities such as OR, OCOR, NCOR and the like that fits within the pocket and optionally plus an electron donating group able to enhance the activity of such groups, such as halogen, and $X_3$ is any small size substituent to fit within the pocket, for example a group such as fluorine. In the embodiment of the invention, a structural difference between the molecules of the invention and geldanamycin antibiotics and derivatives is the interaction between these binding moieties and the hydrophobic lateral binding site and small hydrophobic binding site. As observed in Stebbins et al., these sites are located at the bottom of the pocket, and geldanamycin does not fill these portions. Rather, the methyl group of geldanamycin extends only partly into the lateral pocket, leaving room at the bottom of the pocket for water molecules. In contrast, in compositions of the invention, the substituents may be selected to fill at least the hydrophobic lateral binding site in the pocket. As used in this application, the term "fill" refers to the occupancy of a binding site to an extent such that there is not room remaining to accommodate a water molecule.

Figure 5:
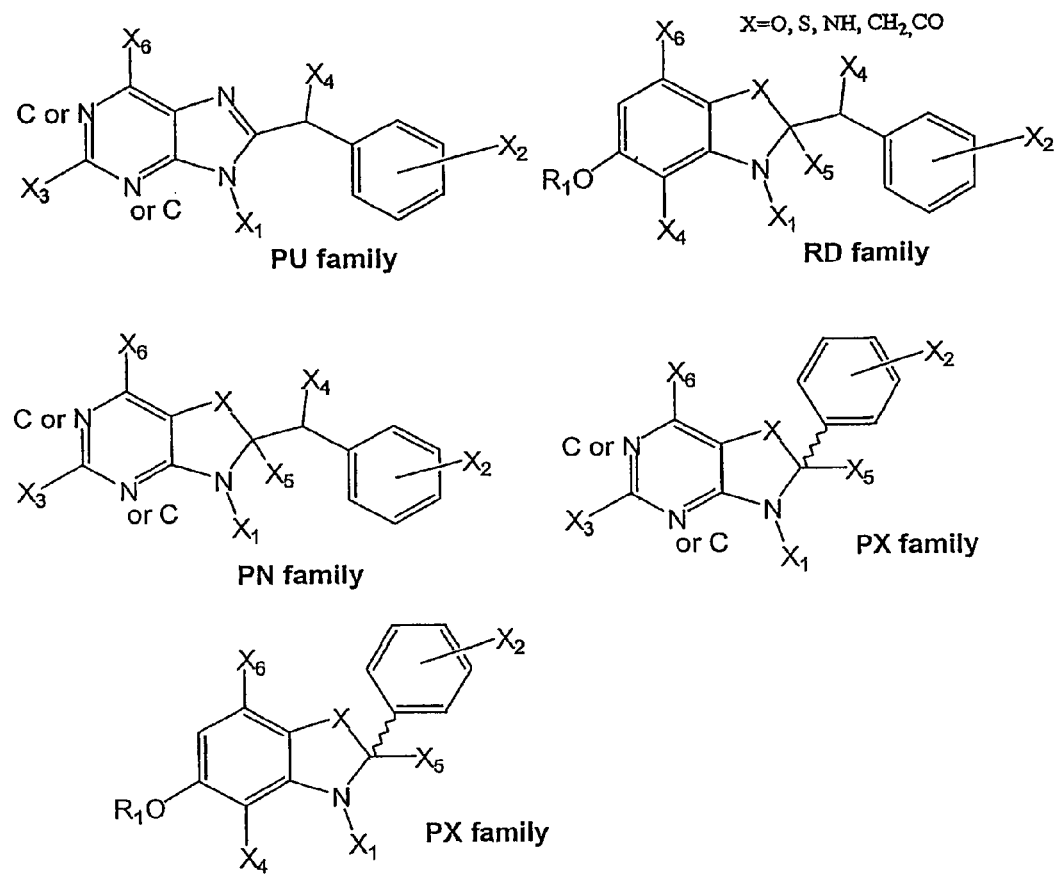
FIG. 5 shows the structure of compounds in accordance with the invention.

Additional examples of binding moieties within the scope of the invention that are designed to fit within the N-terminal pocket of HSP90 proteins and interact with the pockets with affinity between that of ADP and geldanamycin for at least one member of the HSP90 family are shown in FIG. 5. In these compositions, $X_1$ is a hydrophobic chain (linear, branched aliphatic, aromatic, acyclic or cyclic, containing C, H, N, O and/or S atoms that first within the pocket), or COR, where R is a hydrophobic chain; $X_2$ is from 1 to 5 hydrogen acceptor/donor functionalities, which may be the same or different; $X_3$ is a small size group such as alkyl (saturated, unsaturated, cyclic or linear), alkoxy (for example methoxy or ethoxy), halogen or SR (where R is methyl or ethyl); $X_4$ is H or as $X_3$, $X_5$ is H or as $X_1$; $X_6$ is —$NH_2$, —OR (R being H or alkyl), or —$CONH_2$ or a similar hydrogen donor functionality and $R_1$ is H or alkyl. These molecules are all capable for folding into a C-shaped configuration and interact with at least three of the potential binding sites, including the hydrophobic lateral site. It will be appreciated that other compounds with different nuclei but comparable overall volume (~200-500 Å$^3$) and dimensions can be designed in the same manner and fall within the scope of the present invention.

Figure 6A:
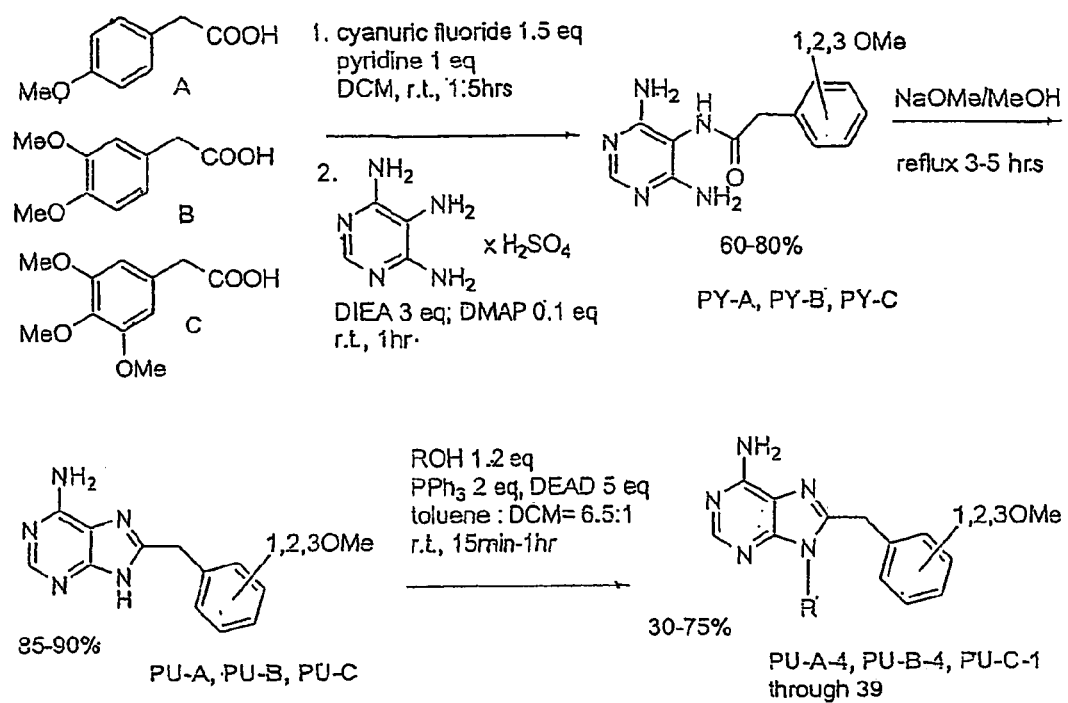
FIG. 6A shows a synthetic procedure for making compounds in accordance with the invention.

The compositions having structures indicated as the PU family in FIG. 5 can be synthesized using the procedure outlined in FIG. 6A. A carboxylic acid starting material is converted to an acid fluoride by reaction with cyanuric fluoride in pyridine/DCM or to an acid chloride by reacting with $SOCl_2$. This acid halide is reacted with an amino-substituted pyrimidine (such as 4,5,6-triaminopyrimidine sulfate in DIEA/DMF or 2,4,5,6-tetraaminopyrimidine sulfate in aqueous NaOH, or either sulfate with $K_2CO_3$ in DMF) to produce an intermediate product (PY-A, PY-B, PY-C in FIG. 1) which undergoes ring closure to produce substituted 8-benzyl purine derivatives (PU-A, PU-B, PU-C) which are useful compositions in accordance with the invention. If desired, a alkylation reaction, such as a Mitsonobu alkylation, may be performed to add an alkyl group, R, (with or without functional substituents) to the nitrogen at the 9-position. Exemplary compounds made by 9-N alkylation of the PU family precursor PU-C are shown in FIG. 6B.

In some embodiments of the invention, the compound has the formula

Figure 6B:
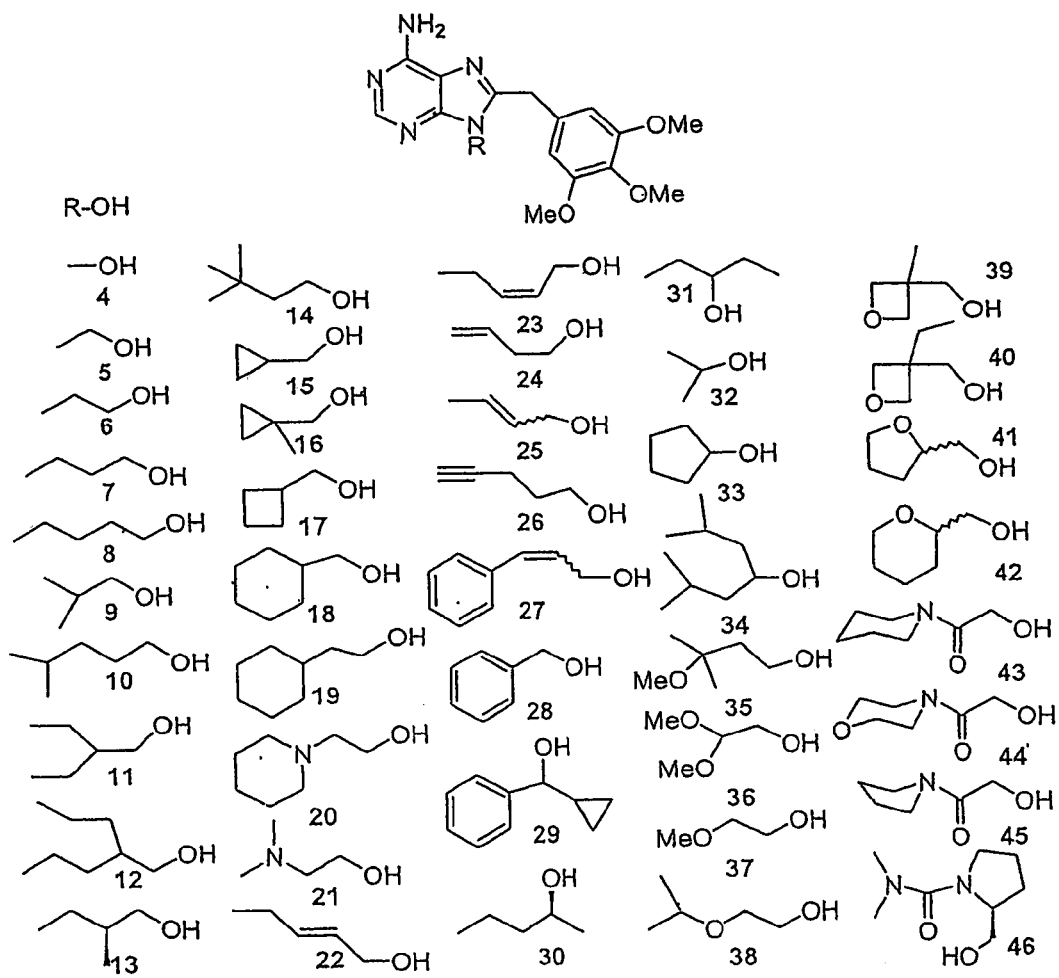
FIG. 6B shows exemplary 9-N alkylation compounds that were tested for activity. As reflected in Table 1, not all of the tested compounds were active, and some of the compounds could not be tested for activity because they were insoluble.

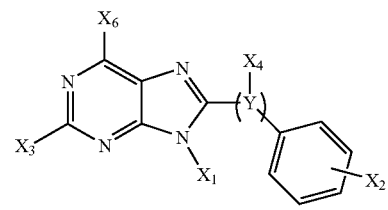

wherein Y is CH, O, N or O—CH, $X_1$ is the substituent formed by removing the OH from an alcohol from FIG. 6B selected from the group consisting of

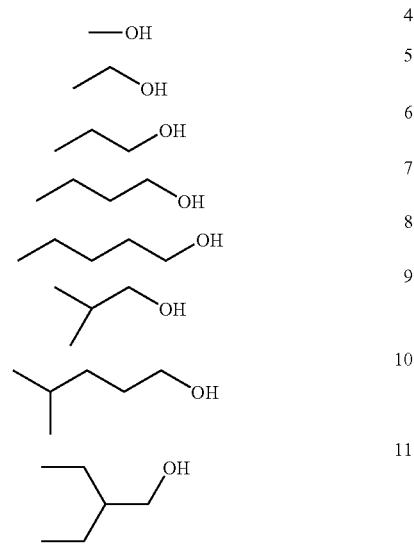

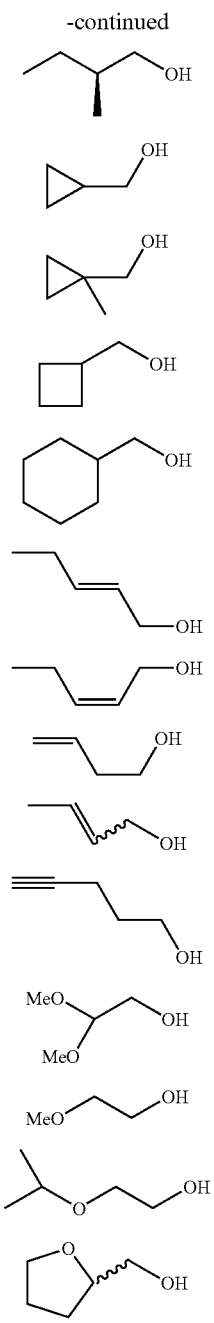

$X_2$ is from one to five non-hydrogen groups independently selected from the group consisting of halogen and methoxy, $X_3$ is halogen, $X_4$ is absent when Y is O or hydrogen, halogen, alkyl, alkoxy, or —$SCH_3$ or —$SCH_2CH_3$, and $X_6$ is —$NH_2$, —OH, —O-Alkyl, or —$CONH_2$.

Figure 7A:
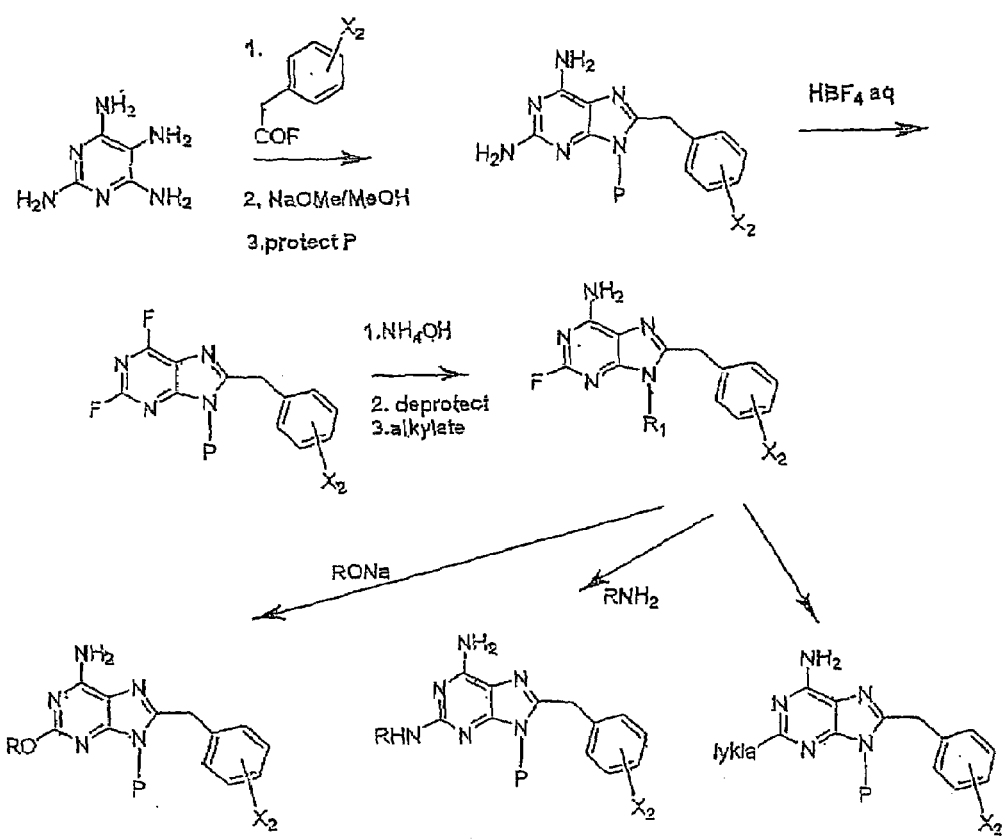
FIG. 7A shows a synthetic scheme for introduction of functional groups at the X3 position for interaction with the small hydrophobic binding site.

FIGS. 7A and B show synthetic schemes for introduction of functional groups at the X3 position for interaction with the small hydrophobic binding site. FIGS. 8A and B show synthetic schemes for introduction of variations at the X2 site.

Figure 9:
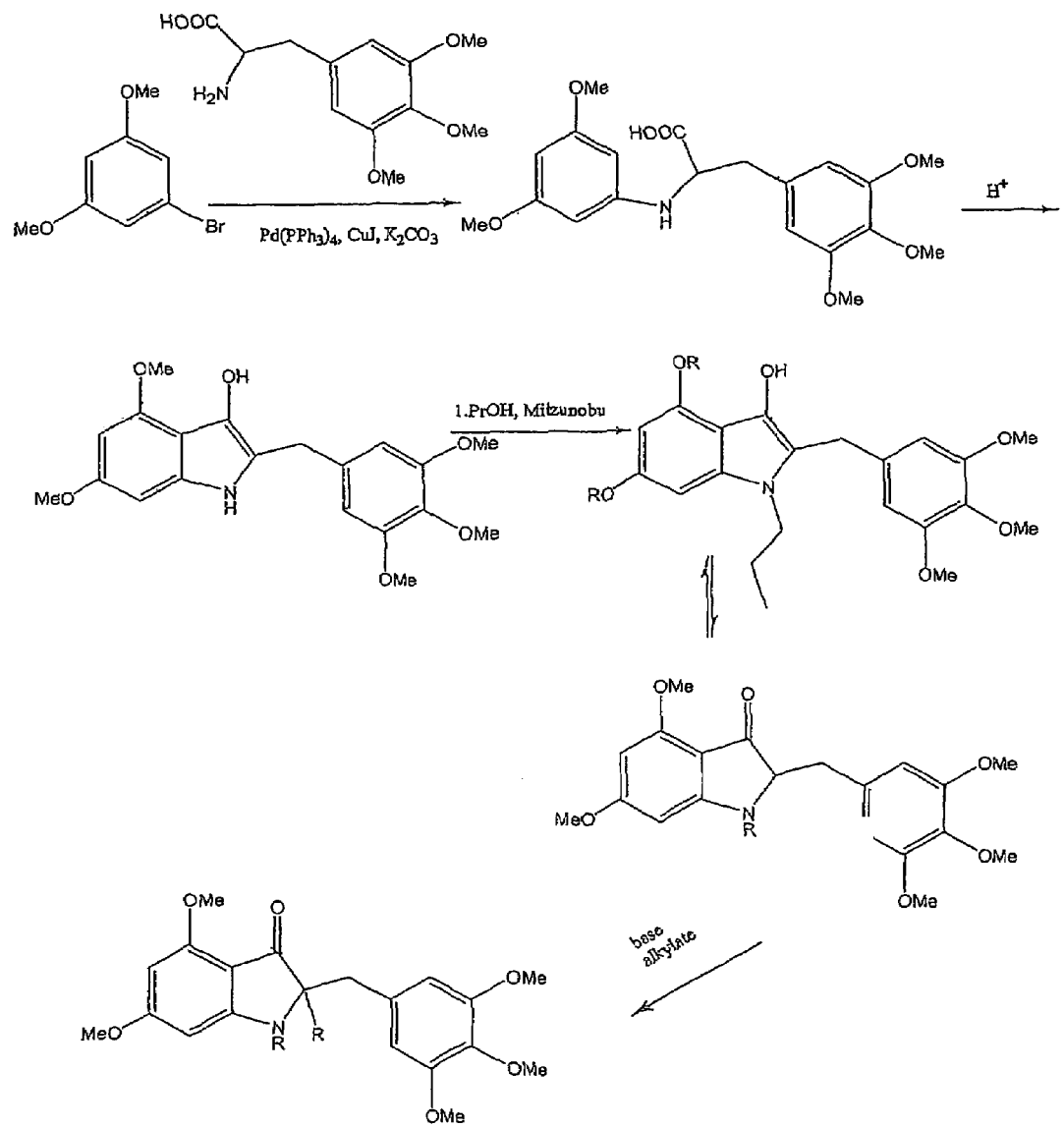
FIG. 9 shows a synthetic scheme for production of binding moieties in accordance with the invention.

FIG. 9 shows a synthetic scheme for synthesis of the RD class of compounds from FIG. 5. Other classes shown in FIG. 5 can be made using comparable synthetic approaches.

The compositions of the invention may be used directly to provide therapeutic benefits in the treatment of cancers and other diseases. As illustrated in the examples below, the compositions of the invention have been shown to induce degradation in Her2 kinase in SKBr3, MCF-7 and BT474 breast cancer cells. In addition, compositions of the invention have been shown to be effective at causing Rb-positive SKBr3 and MCF-7 breast cancer cell lines to undergo G1 arrest, and to have antiproliferative effects against these cell lines and BT474, MDA-MB468 and prostate cancer cell lines TSUPr and LNCaP.

The compounds of the PU family were tested for binding to Hsp90, degradation of Her2 total protein and for their antiproliferative effect. Table 1 summarizes the influence of the 9-N chain on this activity. Compounds of the PU family (FIG. 6) not listed in the table were either inactive or insoluble.

Figure 7B:
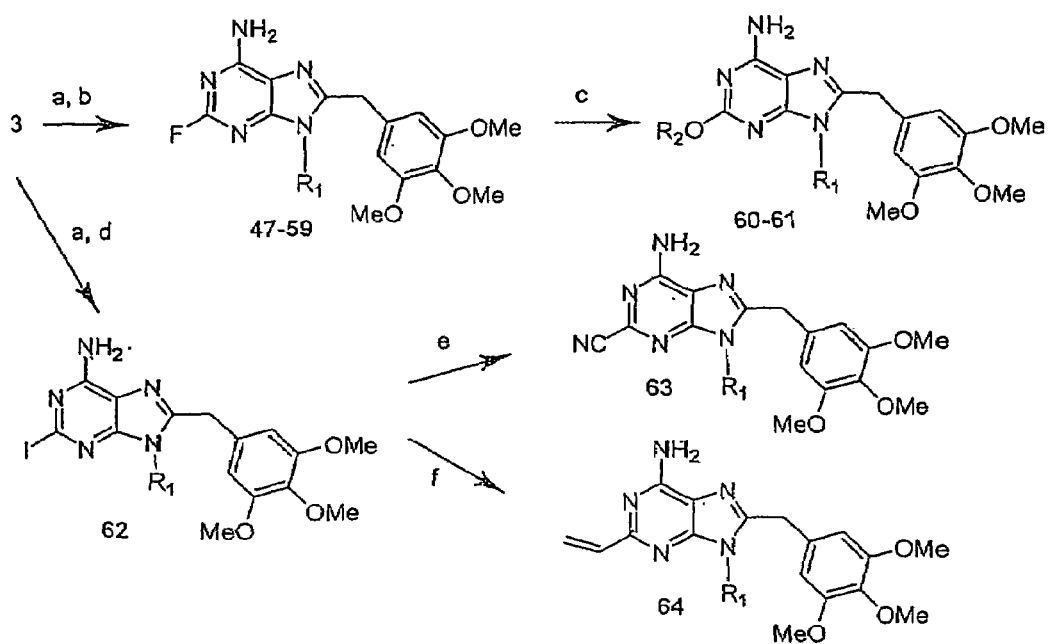
FIG. 7B shows a second synthetic scheme for introduction of functional groups at the X3 position for interaction with the small hydrophobic binding site.

Compounds of the PU family were modified by addition of a fluorine group as substituent X3 (C-2 fluorination) using the reaction protocol of FIG. 7B. The results are summarized in Table 2. As shown, introduction of a fluorine substituent increased the activity of compositions with common X1 groups, and enhanced the activity/solubility of compositions with X1 substituents for which activity was not reported in Table 1.

Figure 8B:
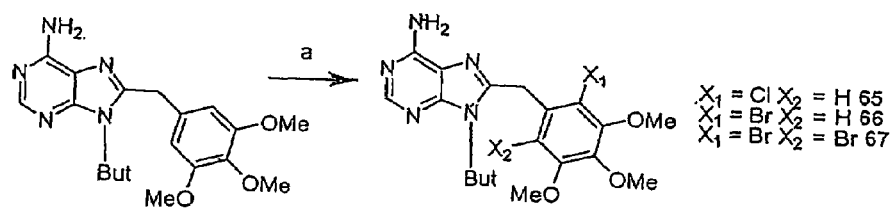
FIGS. 8A and B show synthetic schemes for introduction of variations at the X2 site.

Variations in activity were also observed when additional halogen substituents were added to the phenyl ring using the reaction scheme shown in FIG. 8B. As shown in Table 3, introduction of a halide at one, but not both of the positions not occupied by methoxy groups in PU3 led to an increase in activity relative to PU3.

Compounds were prepared with the chlorine substituent as in compound PU3PhCl and the fluorine substituent as in PU24F or PU29F. As shown in Table 4, these compounds were the most active of those tested so far.

Figure 10:
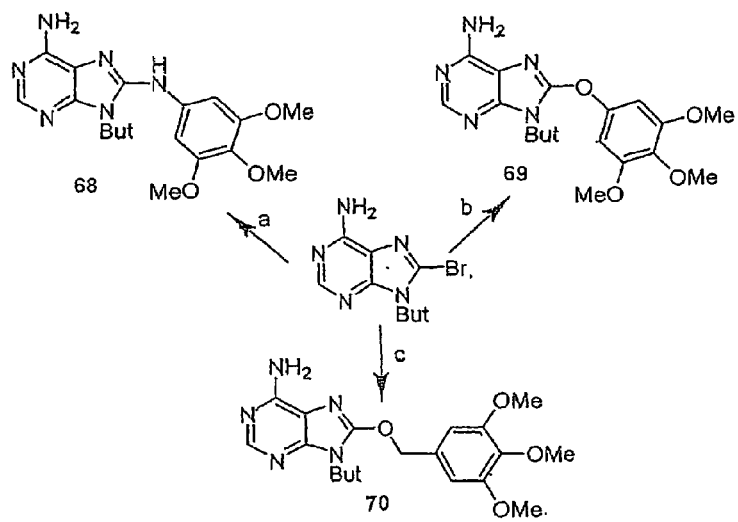
FIG. 10 shows a synthetic scheme for introducing variations in the length and character of the bridge between the purine and the phenyl groups in PU family compounds.

Another location of potential variation in the PU family of molecules is in the length and character of the bridge between the purine and the phenyl groups. FIG. 10 shows a synthetic scheme for achieving such variation. Compound 69 was tested and was found to have weak binding to hsp 90-beta, but no detectable binding to hsp 90-alpha. This is the reverse of the binding selectivity observed for Compound 18. This provides for selectivity between these two proteins.

As an alternative to the use of the compositions of the invention individually, coupled-compositions in which the hsp-binding nucleus as shown in general structures in FIG. 5 are derivatized by coupling to targeting moiety selected to specifically bind to a protein, receptor or marker found on a target population of cells or it may be dimerized. (See FIG. 11) The targeting moiety may be a hormone, hormone analog, protein receptor- or marker-specific antibody or any other ligand that specifically binds to a target of interest. Particular targeting moieties bind to steroid receptors, including estrogen and androgen and progesterone receptors, and transmembrane tyrosine kinases, src-related tyrosine kinases, raf kinases and PI-3 kinases. Specific tyrosine kinases include HER-2 receptors and other members of the epidermal growth factor (EGF) receptor family, and insulin and insulin-like growth factor receptors. Examples of specific targeting moieties include estrogen, estradiol, progestin, testosterone, tamoxifen and wortmannin. Targeting moieties may also be antibodies which bind specifically to receptors, for example antibodies which bind to Her2 receptors as disclosed in International Patent Publications Nos. WO96/32480, WO96/40789 and WO97/04801, which are incorporated herein by reference.

Because of their ability to bring about the degradation of proteins which are essential to cellular function, and hence to retard growth and/or promote cell death, the hsp-binding compounds of the invention, with or without a targeting moiety, can be used in the therapeutic treatment of a variety of disease conditions. A suitable therapeutic is one which degrades a kinase or protein that is found in enhanced amounts or is mutated in disease-associated cells, or on which the viability of such cells depends. The general role of HSP90 proteins in maintaining malignancy in most cancer cells points to the importance of this target in the development of anticancer agents. Thus, the therapeutic small molecules of the invention provide a novel modality for the treatment of all cancers that require or are facilitated by an HSP90 protein. For example, the compositions of the invention can be used in the treatment of a variety of forms of cancer, particularly those that overexpress Her2 or mutated or wild type steroid receptors, or that lack functional RB protein. Such cancers may include but are not limited to breast cancer and prostate cancer. In addition, the compositions of the invention can be used in the treatment of other diseases by targeting proteins associated with pathogenesis for selective degradation. Examples of such targetable proteins include antigens associated with autoimmune diseases and pathogenic proteins associated with Alzheimer's disease.

The compositions of the invention are suitably utilized to degrade specific proteins which are associated with the disease state or condition of concern. Because the compositions of the invention can be selected to degrade specific kinases or signaling proteins, a suitable therapeutic is one which degrades a kinase or protein that is found in enhanced amounts in diseased cells. Thus, for example, the selection of a binding moiety which degrades Her2 kinase, but not other HER kinases or Raf kinase would be suitable for treatment of Her2-positive breast cancer. The examples below provide guidance on the selection of specific compounds based on the specificity observed in vitro. In addition, screening techniques are described below to facilitate the evaluation of structures for binding affinity and differential degradation.

The compositions of the invention are administered to subjects, including human patients, in need of treatment, in an amount effective to bring about the desired therapeutic result. A suitable administration route is intravenous administration, which is now commonly employed in chemotherapy. In addition, because the compositions of the inventions are small soluble molecules, they are suitable for oral administration. The ability to use an oral route of administration is particularly desirable where it may be necessary to provide treatment of a frequent, for example a daily schedule. The amount of any given composition to be administered, and the appropriate schedule for administration are determined using toxicity tests and clinical trials of standard design, and will represent the conclusion drawn from a risk benefit analysis. Such analyses are routinely performed by persons skilled in the art, and do not involve undue experimentation.

Figure 12:
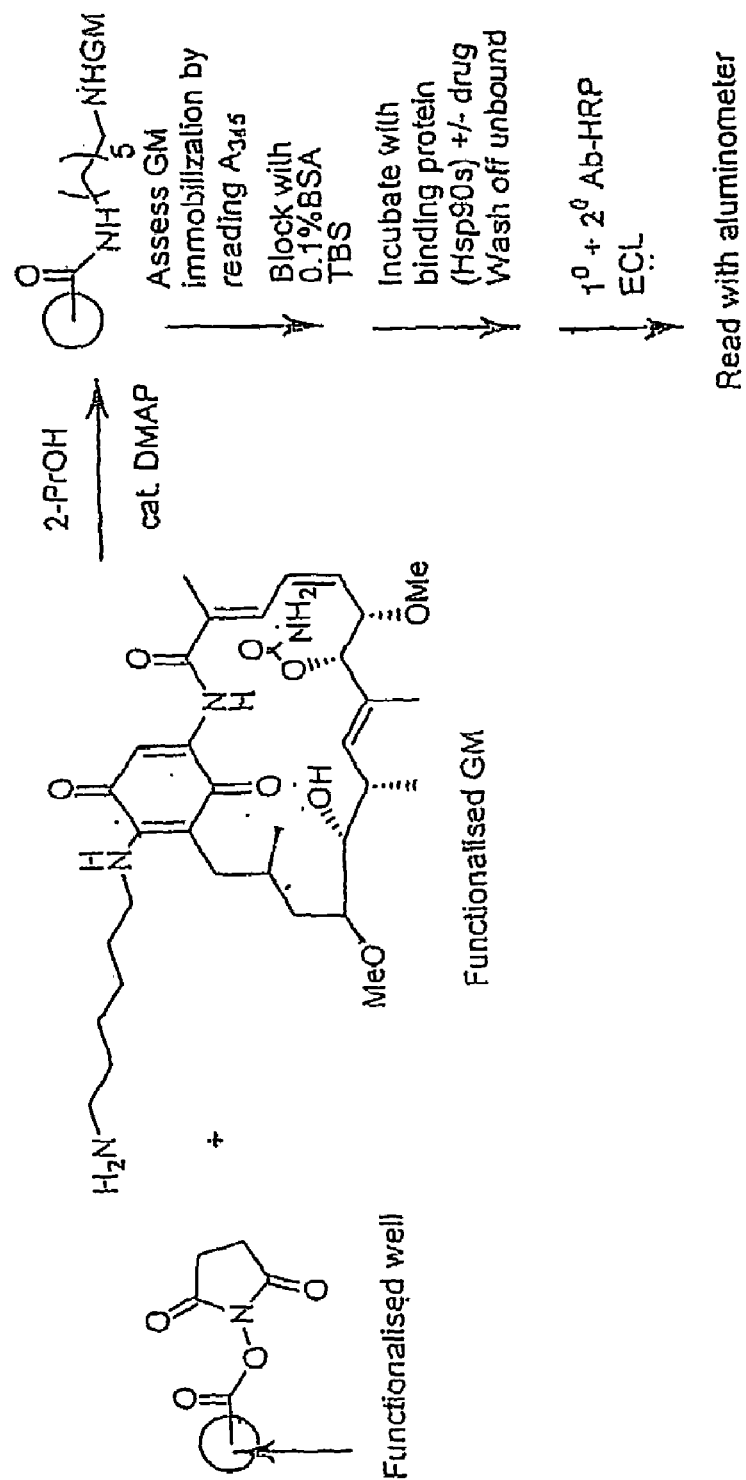
FIG. 12 shows a schematic methodology for assessing comparative affinities of binding moieties.

As an alternative or adjunct to the design of molecules for use as binding moieties in accordance with the invention, we have developed a fast screening assay which can be used to test compounds for their binding affinity to the N-terminal pocket of HSP90, or to test proteins for the presence of an HSP90 type of pocket. As summarized in FIG. 12, the surface of a solid substrate (such as a the bottoms of 96 well microtiter plates) are functionalized with N-oxysuccinimydyl functionalities. These react in isopropanol with amino-functionalized GM (or other ansamycin antibiotic). The amount of GM bound to the wells can be assessed by spectrophotometric absorbance measurements at 345 nm. When the bound GM is incubated with rabbit reticulocyte lysates, enough hsp90 is captured to be detectable by colorimetric methods, although more specific detection methods are preferred. For example, bound hsp90 can be detected using a labeled anti-HRP antibody. To assay for HSP90 binding efficacy, a test compound is added to the wells with the rabbit reticulocyte lysate (or other hsp90 source) and any differences in the amount of captured hsp are noted. If the test compound binds hsp90 with greater affinity than GM, it will compete with the immobilized GM and result in a reduction in the amount of hsp90 captured. By varying the member of the HSP90 family used in the assay, these same plates can be used to evaluate differences in specificity of test compounds. The plates can also be used to screen protein/peptide libraries for proteins which possess an HSP90 type of binding pocket.

A test was also designed which allows identification of compounds which interact differentially with Hsp90-alpha and Hsp90-beta. In this test, geldanamycin (or other strong non-discriminating hsp90 binder such as other ansamycin antibiotics or radicicol) is modified as necessary and affixed to a solid support, for example beads. An Hsp90 protein preparation containing both the alpha and the beta form is incubated with the support in the presence or absence of a compound to be evaluated. If the compound binds to the Hsp90 protein, it competitively inhibits the binding of the protein to the solid support. After washing, the material bound to the support is eluted and the eluate is separated on an SDS/PAGE gel and visualized by immunoblotting with anti-Hsp90-alpha and anti-Hsp90-beta to determine the amount of material bound. Alternatively, if quantitative amounts of the Hsp90 protein preparation or known ratios of alpha to beta forms of Hsp90 are used in the first instance, the unbound material can be analyzed by a similar technique.

Candidate compounds in accordance with the invention can also be evaluated for their ability to deplete or induce proteins which are found in enhanced amounts in cancer cells or on which the cells depend for viability (for example Her2, Her3, Raf-1, ER, Rb, cdk-4, Hsp90, Trap-1, and Grp94) in a panel of cancer cell lines using the cell-based assay of Stockwell et al., *Chem Biol*. 6: 71-83 (1999). In this assay, cells are grown at the bottom of a well and fixed. The fixed cells are probed for the presence of a specific primary antigen (the oncogenic protein) using a specific primary antibody in solution. A secondary antibody covalently linked to horseradish peroxidase is added, and the resulting complex is detected through the chemiluminescent reaction caused by the addition of luminol, hydrogen peroxide and an enhancer such as p-iodophenol. Differences in the detected luminescence levels in the presence of a drug indicate activity of that drug with respect to the degradation or induction of the targeted protein.

Drugs may also be assayed based upon observed very characteristic changes in cell morphology. MCF-7 cells exposed to PU3 flatten, increase in size and have distinct cellular boundaries. The increase in size is mostly due to an abundance in cytoplasm. These morphological changes are characteristic of mature epithelial differentiation and reversal of transformation.

As a third alternative, Immunofluorescence (IF) and Hematoxylin and Eosin stain (H&E) may be used to assess drug effectiveness. Cells were plated on 8 well chamber slides, Fisher Scientific) and seeded for 24 hrs. Drugs or vehicle were added for 5 days after which, for IF the slides were washed twice with ice-cold PBS and fixed with methanol and acetone solution (1:1) for 15 sec. Fixed monolayers were washed with distilled water and blocked with 5% BSA in PBS solution. After blocking, cells were incubated with the primary antibody (anti-MFMG, Chemicon, 1:100 in 5% BSA in PBS) at 37° C. and washed 3 times with 1% BSA in PBS, followed by incubation with a rhodamine-labeled secondary antibody for 1 hr at 37° C. Nuclei were stained with DAPI at 1 mg/ml. For H&E, the cells were fixed with paraformaldehyde (4%) for 10 min at RT and stained according to standard H&E staining protocols. The induction of G1 arrest by a variety of manipulations is sufficient for induction of expression of some milk proteins. However, only ansamycin, the HDAC inhibitor SAHA and the hsp90 binding molecules cause extensive morphological and biological changes.

For use in the therapeutic method of the invention, the compositions of the invention are formulated in a pharmaceutically acceptable carrier. For injectable formulations, this may be a sterile solution (for example sterile saline), or the compounds may be formulated in a lipidic carrier. For oral formulations, the compositions of the invention may be packaged in convenient dosage unit form, for example as tablets or capsules with suitable excipients, or as a liquid formulation. In the latter case, the liquid pharmaceutical will suitably include a flavorant to enhance palatability, and may also include colorants and other conventional additives.

EXAMPLE 1

Compositions having general formula 1 were synthesized according to the scheme shown in FIG. 6A. To generate acid fluorides, to a solution of the phenyl acetic acid derivative (3 mmol) in 15 mL of $CH_2Cl_2$ (under inert atmosphere) were added 1.5 equivalents of cyanuric fluoride and pyridine (3 mmol). The mix was stirred for 1.5 h at room temperature, after which, 30 more mL of $CH_2Cl_2$ were added. The resulting solution was washed once with 0.5 mL water, and the crude acid fluoride material resulted from the removal of the solvent was used in the next step.

The acid fluoride was used for the generation of PY-A, PY-B and PY-C derivatives as follows: To 675 mg (2.8 mmol) of 4,5,6-triaminopyrimidine sulphate in 1.5 mL of DMF were added 1.5 mL (9 mmol) of DIEA, the acid fluoride (obtained as described above) dissolved in 5 mL $CH_2Cl_2$ and a catalytic amount of DMAP (0.28 mmol). The reaction mixture was stirred under argon for 1 hr. The solid that formed was filtered off and the filtrate was concentrate to dryness. To the residue material was added 10 mL EtOAc and the precipitate formed was washed several times with EtOAc and $CH_2Cl_2$ to give a slightly yellow material in 60-80% yield. This material was used for the next step. If higher purity is desired, flash chromatography using EtOAc: MeOH=7:1 (1% TEA) can be performed.

From the PY compounds, PU-A, PU-B and PU-C derivatives were generated as follows: To 500 mg (1.5 mmol) of 5-acylated-4,5,6-pyrimidine in 13 mL MeOH was added 13 mL solution of 25% NaOMe in MeOH and the resulting solution was refluxed for 5 hrs. After cooling, 5 mL of water was added and the solution was concentrated to 5 mL. The resulting aqueous solution was extracted with 4×10 mL THF and 2×10 mL EtOAc. The combined organic layers were dried with $MgSO_4$, concentrated to dryness to give a slightly yellow solid in 80-90% yield. If higher purity is desired the resulting product can be added to a silica gel column and eluted with $CH_2Cl_2$:EtOAc:MeOH=4:4:1.

Substituents were added to the 9-N position using a Mitsunobu alkylation as follows: To 0.16 mmol of purine derivative in 5 mL toluene and 1 mL $CH_2Cl_2$ were added 2.2 equivalents $PPh_3$ and 1.3 equivalents of ROH followed by 5 equivalents of DEAD. The reaction was monitored by TLC and proceeded in 15 min to 1 hr. The mixture was applied to a ISCO CombiFlash system (silica gel column) and eluted with a gradient of $CH_2Cl_2$/acetone to give 30-75% isolated product. This procedure was carried out using the 40 unbranched and branched, linear and cyclic, saturated and unsaturated primary and secondary alcohols shown in FIG. 6.

In these syntheses, only two alcohols, neopentyl alcohol and cyclohexanol, were found to give no product in this reaction.

Figure 13:
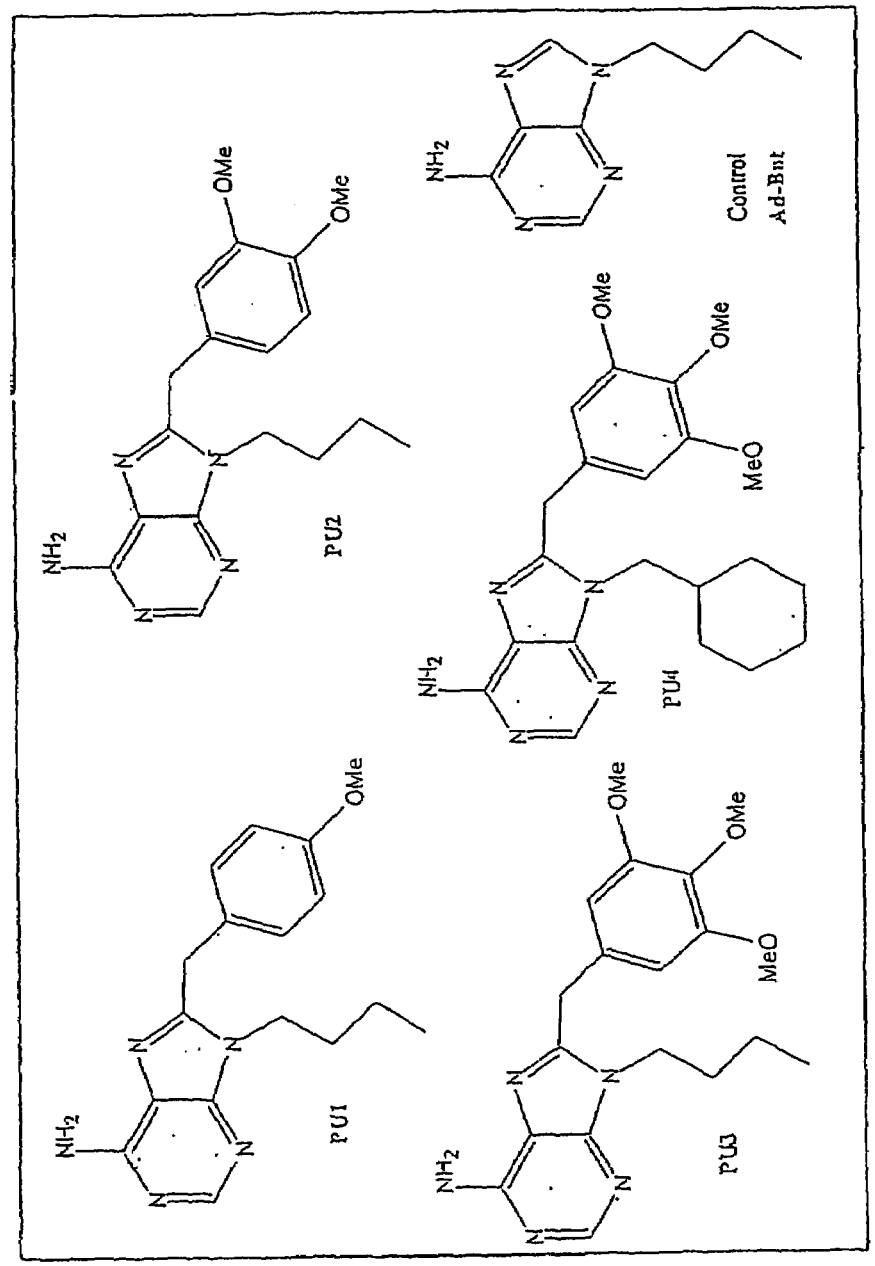
FIG. 13 shows the specific structures of PU1-PU4.

Four of the compounds (PU-A-4, PU-B-4, PU-C-4 and PU-C-15) were used in initial tests. For convenience, these four structures are referred to as PU1, PU2, PU3 and PU4, respectively as shown in FIG. 13.

EXAMPLE 2

The human cancer cell lines MCF-7, SKBr3 and MDA-MB-468 were obtained from the American Type Culture Collection (Manassas, Va.) and maintained in 1:1 mixture of DME:F12 supplemented with 2 mM glutamine, 50 units/mL penicillin, 50 units/mL streptomycin and 5% (for MCF-7 and MDA-MB-468) or 10% (for SKBr3) heat inactivated fetal bovine serum (Gemini Bioproducts) and incubated at 37° C. in 5% $CO_2$.

For assays on protein levels, cells were grown to 60-70% confluence exposed to drugs or DMSO vehicle for the indicated time periods. Lysates were prepared using 50 mM Tris pH=7.4, 2% SDS and 10% glycerol lysis buffer. Protein concentration was determined using the BCA kit (Pierce Chemical Co.), according to the manufacturers instructions. Clarified protein lysates (20-50 mg) were electrophoretically resolved on denaturing SDS-PAGE, transferred to nitrocellulose and probed with the following primary antibodies: anti-Her2 (C-18), -Her3 (C-17), -Raf-1, -cyclin D1, -Rb (C-15) (Santa Cruz), anti-hsp90, -hsp70, -ER (Stressgen), anti-Trap-1 (MSK81), anti-b-actin, -tubulin (Sigma), anti-PI3K (p85) (Upstate Biotechnologies).

To determine antiproliferative indices, growth assays were performed by seeding 10,000 cells per well in 6-well dishes and incubating for 24 hrs before drug treatment. Drugs or vehicle were administered as outlined for each experiment, and cells were incubated for the time periods depicted and then counted by coulter counter.

Cell cycle distribution was assayed according to Nusse et al with a Becton Dickinson fluorescence activated cell sorter and analyzed by Cell Cycle Multi-cycle system (Phoenix Flow System, San Diego, Calif.).

Experiment 1

MCF-7 cells were treated with varying concentrations (0, 10, 50, 100 or 250 µM of PU3 or the control purine Ad-But for 24 hours and then lysed. Levels of Hsp90, Trap1 and Hsp70 were evaluated by Western blotting. The results showed that PU3, like GM, increases the cellular levels of Hsp90 and Hsp70. Treatment of cells with PU3 also induces a protein band that migrates more rapidly than Trap-1 and that is recognized by an anti-Trap-1 antibody. Although the identity of this protein band is unknown, its appearance seems to be a marker of cellular exposure to Hsp90 inhibitors. Ad-But had no effect on the studied protein levels at identical concentrations.

Experiment 2

Cell cultures of MCF-7, SKBr3 and MDA-MB-468 cells were treated with PU3 at one of several concentrations or a DMSO control to test for the occurrence of antiproliferative effects. FIGS. 14A-C show the results of cell number as a function of time. As shown, PU3 clearly inhibits growth of these breast cancer cell lines.

Experiment 3

Cell cultures of SKBr3 cells were treated with PU1, PU2, PU3 or PU4 at concentrations of 0, 10, 50, 100 and 250 µM. After 24 hours, the cells were lysed and the amount of Her2 and Raf-1 in the cells was evaluated. Although the compounds are structurally very similar, they were found to have different efficacy at promoting degradation of the two proteins. PU1 showed little degradation of either protein at any of the concentrations tested, while PU2 degraded Her2 but not Raf-1 at 250 µM. PU3 degraded Her2 at concentrations over 100 µM but resulted in only partial loss of Raf-1 at 250 µM. PU4 degraded Her2 at concentrations greater than 50 µM and Raf-1 at a concentration of 250 µM.

Experiment 4

To test the time course of degradation, MCF-7 cells were treated with 100 µM PU3. Aliquots of cells were recovered at 1.5, 3, 6, 12 and 24 hours, and the amount of Her2, Raf-1, Hsp90 and Trap-1 was evaluated. The compound was shown to induce rapid degradation of Her2 (with more than 50% being lost within 3 hours of adminstration) and significant synthesis of Hsp90 and Hsp70 within the 24 hour period. The amount of Raf-1 did not change significantly during this time.

Experiment 5

Cell cultures of MCF-7 cells were treated with PU1, PU2, PU3 or PU4 at concentrations of 0, 10, 50, 100 and 250 µM. After 24 hours, the cells were lysed and the amount of Her2 in the cells was evaluated. Although the compounds are structurally very similar, they were found to have different efficacy at promoting degradation of Her2. PU1 showed only partial degradation at concentrations in excess of 50 µM, while PU2 degraded Her2 completely at 250 µM. PU3 substantially degraded Her2 at concentrations over 10 µM. PU4 substantially degraded Her2 at concentrations greater than 100 µM.

Experiment 6

Cell cultures of MCF-7 cells were treated with PU1, PU2, PU3 or PU4 at concentrations of 0, 10, 50, 100 and 250 µM. After 24 hours, the cells were lysed and the amount of estrogen receptor in the cells was evaluated. Although the compounds are structurally very similar, they were found to have different efficacy at promoting degradation of estrogen receptors. PU1 showed essentially no degradation at the concentrations tested, while PU2 degraded estrogen receptor completely at 250 µM. PU3 partially degraded estrogen receptor at concentrations over 50 µM. PU4 substantially degraded Her2 at concentrations greater than 100 µM.

Experiment 7

Cultures of SKBr3 and MCF-7 cells were treated with varying concentrations (0, 10, 50 100, or 250 µM) of PU3 for 24 hours. The cells were lysed and levels of Her2, Raf1, Her3, estrogen receptor (ER), p85 (PI3K), tubulin and actin were analyzed by western blotting. Reduction in the amount of those signaling proteins which depend on hsp90 for their function (Her2, Raf1, Her3 and ER) was observed. No effect was observed on PI3K, tubulin or actin, proteins which are involved in other signaling pathways.

EXAMPLE 3

The experiments of Example 2 demonstrate the ability of synthetic compounds PU1, PU2, PU3 and PU4 in accordance with the invention to provide differential degradation of kinases HER3, estrogen receptor (ER), Her2, Raf, Rb and p85 (as reference protein which should not be, and is not degraded). Several important observations can be made from this data.

PU3 destabilizes the estrogen receptor complex and induces dose-dependent degradation of the protein. PU3 also causes a rapid decrease in Her2 levels and causes accumulation of a lower-molecular weight (170 kDa versus 180 kDa mature protein) HER-2 band, also seen for GM, that is thought to be incompletely glycosylated Her2 which is sequestered in vivo in the endoplasmic reticulum. Levels of Raf and Her3 are less sensitive to PU3, but are degraded at higher concentrations. PU2 also induces a lower molecular weight Rb band which is thought to be hyperphosphorylated Rb.

In contrast, PU2 showed substantial degradation of Her2 without accumulation of the lower molecular weight band and was less effective for degradation of Raf kinase. The lower molecular weight band is also absent when PU1 is used as the binding moiety. PU2 is less effective at degrading ER, while PU1 was had substantially no affect on ER. These differences provide evidence suggesting that PU3 binds to a different member of the HSP90 family from PU1 and PU2, thus accounting for the different specificity. PU4 also shows greater ability to degrade Her2 than ER or Raf.

EXAMPLE 4

Figure 15:
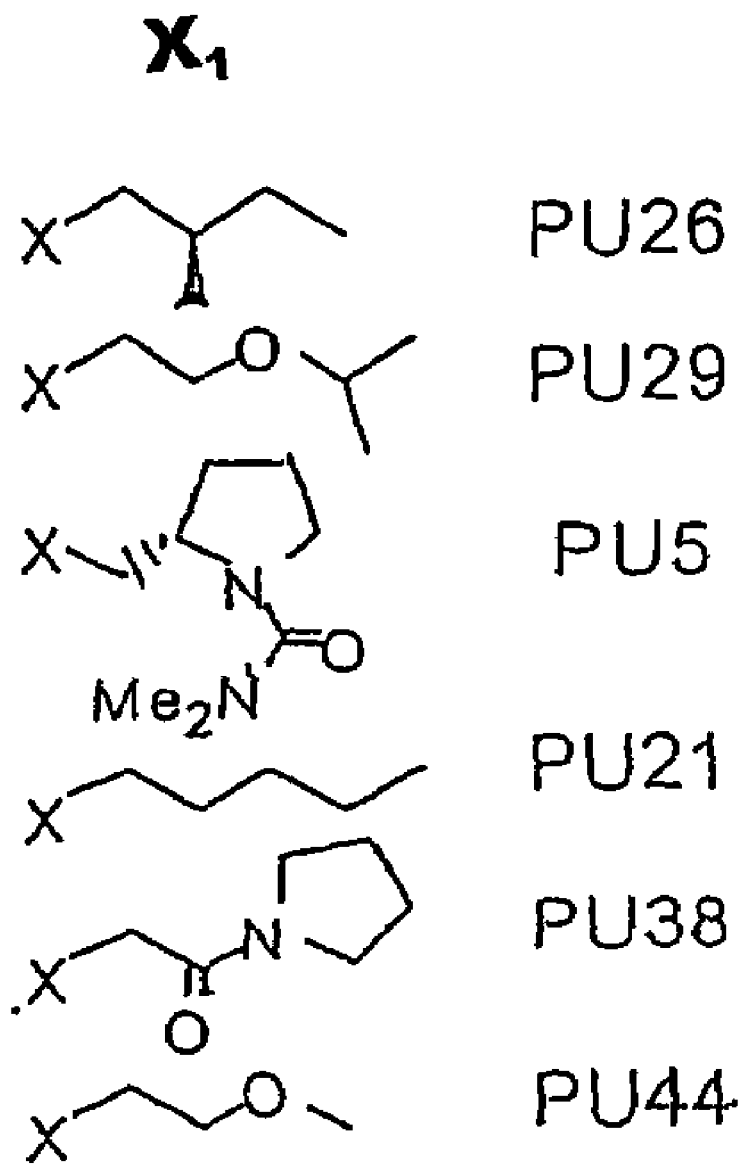
FIG. 15 shows $X_1$ substituents of compounds tested in one example.

Six compounds of the PU-C family (X4=H, X2=1, 2, 3 OMe, X3=H and with variable X1 groups as indicated in FIG. 15) were prepared and tested for their effect on Her2, HER3 and TRAP-1 in MCF-7 cells. The cells were treated for 24 hours with 10, 50, 100 and 250 µM of each compound. The nature and size of the X1 group has a significant effect on the activity of the compound. Large, hydrophobic groups which will better fill the N-terminal pocket show the ability to degrade Her2, but not Her3. In addition, for these compounds there is a correlation between the ability to degrade Her2 and induction of Trap-1 synthesis.

On the other hand, the compounds with big, rigid and somewhat polar X1 groups interact less favorably, and do not significantly degrade Her2 at the concentrations tested.

EXAMPLE 5

PU3 was linked to Biotin through the middle OH in accordance with the synthetic scheme shown in FIGS. 16A and B. PU3-biotin was immobilized on Sepharose-Streptavidin beads. These beads were used to show the interaction of PU3 with the Trap-1 and Hsp90alpha

EXAMPLE 6

PU3 was tested for its safety and potency in MCF-7 xenografts. The compound was administered IP up to 500 mg/kg without showing significant signs of toxicity. Mice with established tumors were treated with a single dose of PU3 at doses of 50, 100 and 500 mg/kg i.p. Control mice were treated with DMSO alone. Mice were sacrificed 12 hours post-treatment. For immunoblotting, tumor tissue was homogenized in 2% SDS lysis buffer (pH 7.4). In all cases a reduction in Her2 levels was observed in the immunoblotting results. No change was observed in levels of PI3 kinase (p85).

EXAMPLE7

Several 9-Alkyl-8-benzyl-9H-purin-6-ylamines (4-46) were created by 9-N-alkylation of PU-C (FIG. 6B). Additionally, the 2-amino group of 3 (FIG. 7B) was converted to fluorine via a diazotization reaction in non-aqueous media using tert-butyl nitrite (TBN) in HF/pyridine. The resulting purine was alkylated to give the 2-fluoro-9-alkyl-8-(3,4,5-trimethoxy-benzyl)-9H-purin-6-ylamines 47-59. The alkylation was performed using the Mitsunobu reaction, methodology that can accommodate a large array of primary and secondary alcohols. The 2-fluoro derivatives were converted to the 2-alcoxy purines 60 and 61 by refluxing in the corresponding alcohol and NaOMe. The majority of modifications at position 2 of the purine moiety commenced with (3). Iodine was introduced in that position using isoamyl nitrite in diiodomethane to give 62. The 2-iodo derivative was transformed to the cyano-derivative 63 with tri-n-butylcyanostannane and tetrakis(triphenylphosphine)palladium(0) in DMF and to the vinyl-derivative 64 with vinyltributyltin and $(MeCN)_2PdCl_2$.

The benzyl moiety was enriched in electron-donating groups in order to increase its interaction with the pocket lysine. Chlorine and bromine were added via a radicalic reaction using t-butyl hydroperoxide and the corresponding acid halide. In the case of chlorine only monosubstitution was observed (65), while bromine gave the monosubstituted (66) and a small amount of di-bromosubstituted product (67). (FIG. 8B)

The nature and length of the bridge between the purine and the phenyl ring were additionally modified. As starting material we utilized the 8-Br-adenine. This was reacted at high temperature with the aniline-, phenol- or benzyl-derivative to give the corresponding products 68-70. (FIG. 10)

The assembly of the fully substituted derivatives 71 and 72 commenced with 3. Chlorine was added initially via the radicalic reaction described above to give 73. Subsequently, the 2-amino group was transformed to fluorine and the resulting purine (74) was alkylated via the Mitsunobu reaction.

Specific reactions for various compounds are set forth below: 3 (DAAC): 8-(3,4,5-Trimethoxy-benzyl)-9H-purine-2,6-diamine: To trimethoxyphenyl acetic acid (1.0 g, 4.4 mmol) in DCM (20 mL) (under inert atmosphere) was added cyanuric fluoride (371 mL, 4.4 mmol) and pyridine (356 mL, 4.4 mmol). The mixture was stirred for 1 h at room temperature, after which, an additional 30 mL of DCM was added. The resulting solution was washed once with water (5 mL), and the acid fluoride resulted from the removal of the solvent was taken up in DMF (10 mL) and used in the next step. Separately, 2,4,5,6-tetraaminopyrimidine sulfate (0.9 g, 3.8 mmol) was dissolved in water (40 mL) that contained NaOH (456 mg, 11.4 mmol). The resulting solution was heated to 70° C. and the acid fluoride was added drop wise over a 20 minute period. The reaction mixture was stirred for 1.5 h at 70° C. and then concentrated to dryness. To the crude material was added MeOH (16 mL) and a 25% solution of NaOMe in MeOH (16 mL) and the resulting solution was heated at 90° C. for 18 h. Following cooling, the pH of the solution was adjusted to 7 by addition of concentrated HCl. The aqueous solution was removed and the crude taken up in DCM (100 mL) and MeOH (50 mL). The undissolved solids were filtered off and the product (470 mg, 37%) was purified on a silica gel column with EtOAc:DCM:MeOH at 4:4:2.

FAC: 2-Fluoro-8-(3,4,5-trimethoxy-benzyl)-9H-purin-6-ylamine: To 3 (500 mg, 1.5 mmol) was slowly added a 70% solution of HF in pyridine (2 mL), pyridine (8 mL), followed by t-butyl nitrite (200 mL, 2.0 mmol). The mixture was stirred for 2 h and then quenched overnight with 8 g $CaCO_3$ in water (15 mL) and MeOH (10 mL). The solution was concentrated to dryness and the resulting crude was taken up in MeOH (30 mL) and DCM (10 mL). The insoluble solids were filtered off and the solvent was removed to give the crude product. This was purified on a silica gel column eluting with hexane:DCM:EtOAc:MeOH at 10:5:5:0.75 (240 mg, 50%).

The alkylation was performed via a Mitsunobu reaction as described before (ref). Essentially, to FAC in toluene:DCM at 5:1 was added 1.3 eq. of the corresponding alcohol, 2 eq. $PPh_3$, 3 eq. di-tert-butyl azodicarboxylate and the resulting solution was stirred at room temperature for 10 min to 1 h (conversion was monitored by TLC) to give:

48 (PU3F): 2-Fluoro-9-butyl-8-(3,4,5-trimethoxy-benzyl)-9H-purin-6-ylamine: 60% yield.

52 (PU29F): 2-Fluoro-9-(2-isopropoxy-ethyl)-8-(3,4,5-trimethoxy-benzyl)-9H-purin-6-ylamine 86% yield.

54 (PU47F): 2-Fluoro-9-pent-4-enyl-8-(3,4,5-trimethoxy-benzyl)-9H-purin-6-ylamine: 86% yield.

59 (PU20F): 2-Fluoro-9-(tetrahydrofuran-2-ylmethyl)-8-(3,4,5-trimethoxy-benzyl)-9H-purin-6-ylamine: 53% yield.

50 (PU44F): 2-Fluoro-9-(2-methoxy-ethyl)-8-(3,4,5-trimethoxy-benzyl)-9H-purin-6-ylamine: 28% yield.

47 (PU43F): 2-Fluoro-9-propyl-8-(3,4,5-trimethoxy-benzyl)-9H-purin-6-ylamine: 66% yield.

57 (PU24F): 2-Fluoro-9-pent-4-ynyl-8-(3,4,5-trimethoxy-benzyl)-9H-purin-6-ylamine: 76% yield.

53 (PU8F): 2-Fluoro-9-but-3-enyl-8-(3,4,5-trimethoxy-benzyl)-9H-purin-6-ylamine: 42% yield.

55 (PU48F): 2-Fluoro-9-but-3-ynyl-8-(3,4,5-trimethoxy-benzyl)-9H-purin-6-ylamine: 36% yield.

56 (PU49F): 2-Fluoro-9-pent-3-ynyl-8-(3,4,5-trimethoxy-benzyl)-9H-purin-6-ylamine: 25% yield.

58 (PU16F): 2-Fluoro-9-cyclobutylmethyl-8-(3,4,5-trimethoxy-benzyl)-9H-purin-6-ylamine: 33% yield.

51 (PU26F): 2-Fluoro-9-[(S)-2-methyl-butyl]-8-(3,4,5-trimethoxy-benzyl)-9H-purin-6-ylamine: 68% yield.

49 (PU21F): 2-Fluoro-9-pentyl-8-(3,4,5-trimethoxy-benzyl)-9H-purin-6-ylamine: 65% yield.

PU24DA: 9-Pent-4-ynyl-8-(3,4,5-trimethoxy-benzyl)-9H-purine-2,6-diamine: To DAAC (200 mg, 0.61 mmol) of in toluene (20 mL) and DCM (4 mL) was added $PPh_3$ (330 mg, 1.3 mmol), 4-pentyne-1-ol (75 mL, 0.8 mmol) and di-t-butyl azodicarboxylate (600 mg, 2.5 mmol). The mixture was stirred at room temperature for 2 h. The product was isolated by column chromatography on a silica gel column eluting with hexane:$CHCl_3$:EtOAc:EtOH at 10:8:4:4 (120 mg solid, 49%).

62 (PU24I): 2-Iodo-9-pent-4-ynyl-8-(3,4,5-trimethoxy-benzyl)-9H-purin-6-ylamine: To PU24DA (50 mg, 0.13 mmol) was added $CH_2I_2$ (2.5 mL) and isoamyl nitrite (100 mL, 0.78 mmol) and the resulting solution was heated at 80° C. for 1 h. After cooling, the solution was concentrated and then added to a silica gel column. The product was isolated (40 mg, 61%) using eluent hexane:$CHCl_3$:EtOAc:EtOH at 10:4:4:0.75.

63 (PU24CN): 2-Cyano-9-pent-4-ynyl-8-(3,4,5-trimethoxy-benzyl)-9H-purin-6-ylamine: A solution of PU24I (20 mg, 0.04 mmol), $Pd(PPh_3)_4$ (7 mg, $6.3 \times 10^{-3}$ mmol) and tributyltin cyanide (14 mg, 0.043 mmol) in dry DMF (2.5 mL) was heated at 180° C. for 6 h. Following cooling and removal of the solvent, the product (13 mg, 81%) was isolated by column chromatography (hexane:$CHCl_3$:EtOAc:EtOH at 10:8:4:0.75).

64 (PU24V): 9-Pent-4-ynyl-8-(3,4,5-trimethyl-benzyl)-2-vinyl-9H-purin-6-ylamine: A solution of PU24I (20 mg, 0.04 mmol), $(MeCN)_2PdCl_2$ ($2 \times 10^{-3}$ mmol) and tributylvinyltin (12.5 mL, 0.041 mmol) in dry DMF (3 mL) was heated at 100° C. for 1 h. Following cooling and removal of the solvent, the product (15 mg, 92%) was isolated by column chromatography (hexane:$CHCl_3$:EtOAc:EtOH at 10:8:4:1).

60 (PU3OMe): 2-Methoxy-9-butyl-8-(3,4,5-trimethoxy-benzyl)-9H-purin-6-ylamine: To a solution of PU3F (20 mg, 0.051 mmol) in MeOH (1 mL) was added a 25% solution of NaOMe in MeOH (1.5 mL). The resulting mixture was heated at 85° C. for 2 h. Subsequent to cooling, the mixture was neutralized with 4 N HCl and then concentrated to dryness. The crude was purified on a silica gel column with hexane:EtOAc:DCM:MeOH at 10:5:5:1 to give a solid (11 mg, 51%).

61 (PU3OEt): 2-Ethoxy-9-butyl-8-(3,4,5-trimethoxy-benzyl)-9H-purin-6-ylamine: To a solution of PU3F (20 mg, 0.051 mmol) in EtOH (2 mL) was added NaOMe (15 mg, 0.28 mmol) and the mixture was refluxed for 2 h. After cooling and neutralization with HCl, the solution was concentrated to dryness. The product (12 mg, 56%) was purified as described above.

65 (PU3Cl): 9-butyl-8-(2-chloro-3,4,5-trimethoxy-benzyl)-9H-purin-6-ylamine: To PU3 (37 mg, 0.1 mmol) in MeOH (3 mL) was added concentrated HCl (33 mL, 0.4 mmol). The solution was cooled to 0° C. and a 90% aqueous solution of t-butyl hydroperoxide (44 mL, 0.4 mmol) was added. The resulting solution was refluxed overnight. Following cooling and removal of the solvent, the product (31 mg solid, 72%) was isolated by column chromatography (elute with hexane:EtOAC:DCM:MeOH at 10:5:5:1.5).

66 and 67 (PU3PhBr and PU3PhBr2): To PU3 (37 mg, 0.1 mmol) in MeOH (3 mL) was added a 48% aqueous solution of HBr (45 mL, 0.4 mmol). The mixture was cooled to 0° C., and t-butyl hydroperoxide (44 mL, 0.4 mmol) was added dropwise. The resulting solution was stirred for 30 minutes at 0° C. and then refluxed for an additional hour. Following cooling and removal of the solvent, the mixture was separated by column chromatography (elute with hexane:EtOAC:DCM:MeOH at 10:5:5:1.5) to give predominantly monobrominated product (31 mg, 69%) and a trace of dibrominated product (2.3 mg, 4.4%). 66 (PU3Br): 9-butyl-8-(2-bromo-3,4,5-trimethoxy-benzyl)-9H-purin-6-ylamine; 67 (PU3Br2): 9-butyl-8-(2,6-dibromo-3,4,5-trimethoxy-benzyl)-9H-purin-6-ylamine.

73 (DAACPhCl): To a slurry of DAAC (1 g, 3.0 mmol) in MeOH (50 mL) was added concentrated HCl (1.5 mL, 18 mmol). The resulting solution was cooled to 0° C. and a 70% aqueous solution of t-butyl hydroperoxide (2.5 mL, 8 mmol) was slowly added. The mixture was stirred for 30 min at 0° C. and then refluxed for 20 h. The solvent was removed under high vacuum to give clean product (1.09 g, 98%).

74 (FDAACPhCl): To a 20% solution of HF in pyridine (6.5 mL) was added (under inert atmosphere) pyridine (13.5 ml), followed by DAACPhCl (1 g, 2.7 mmol). The mixture was stirred for 5 min and consequently, t-butyl nitrite (450 mL, 3.5 mmol) was slowly added. Stirring continued for another 30 min. The reaction was quenched by addition of $CaCO_3$ (16.5 g) in water (10 mL): MeOH (10 mL) and stirring for 2 h. The solution was concentrated and the resulting slurry was taken up in DCM (50 mL): MeOH (50 mL). The insoluble solids were filtered off and washed with DCM:MeOH at 1:1 (2×25 mL). Following solvent removal, the product was purified on a silica gel column eluting with hexane:EtOAc:DCM:MeOH at 10:5:5:1 (370 mg solid, 37%).

71 (PU24FCl): 2-Fluoro-9-pent-4-ynyl-8-(2-chloro-3,4,5-trimethoxy-benzyl)-9H-purin-6ylamine: (308 mg, 76%).

72 (PU29FCl): 2-Fluoro-9-(2-isopropoxy-ethyl)-8-(2-chloro-3,4,5-trimethoxy-benzyl)-9H-purin-6-ylamine:

68 (PAM3): 9-Butyl-N*8*-(3,4,5-trimethoxy-phenyl)-9H-purine-6,8-diamine: A mixture of BrAd3 (50 mg, 0.186 mmol) and trimethoxyaniline (120 mg, 0.65 mmol) was heated at 160° C. for 30 min. Following cooling, the solid was taken up in DCM (20 mL) and MeOH (5 mL) and any insoluble solids were filtered off. The product (57 mg solid, 83%) was purified on a silica gel column eluting with DCM:EtOAc:MeOH at 7:4:1.

70 (PU3OBn): 9-Butyl-8-(3,4,5-trimethoxy-benzyloxy)-9H-purin-6-ylamine: A solution of benzyl alcohol (250 mL, 2.5 mmol) in 25% NaOMe in MeOH (50 mL) was stirred for 5 min. Following the removal of methanol, BrAd3 (26 mg, 0.096 mmol) and Cu powder (10 mg, 0.16 mmol) was added, and the mixture was heated for 2 min at 180° C. The product was purified on silica gel column with hexane: DCM:EtOAc:MeOH at 10:5:5:1 (5.5 mg, 14%).

69 (PU3OPh): 9-Butyl-8-(3,4,5-trimethoxy-phenoxy)-9H-purin-6-ylamine. A mixture of trimethoxyphenol (75 mg, 0.4 mmol), t-BuOK (34 mg, 0.3 mmol), Cu powder (10 mg, 0.64 mmol) and BrAd3 (26 mg, 0.1 mmol) was heated for 1 h at 140° C. The product (13 mg solid, 35%) was isolated by column chromatography (hexane:DCM:EtOAc:MeOH at 10:5:5:1).

EXAMPLE 8

The human cancer cell lines MCF-7, SKBr3 and MDA-MB-468 were obtained from the American Type Culture Collection (Manassas, Va.) and maintained in 1:1 mixture of DME:F12 supplemented with 2 mM glutamine, 50 units/mL penicillin, 50 units/mL streptomycin and 5% (for MCF-7 and MDA-MB-468) or 10% (for SKBr3) heat inactivated fetal bovine serum (Gemini Bioproducts) and incubated at 37° C. in 5% $Co_2$.

Protein Assays. Cells were grown to 60-70% confluence and exposed to drugs or DMSO vehicle for the indicated time periods. Lysates were prepared using 50 mM Tris pH 7.4, 2% SDS and 10% glycerol lysis buffer. Protein concentration was determined using the BCA kit (Pierce Chemical Co.), according to the manufacturers instructions. Clarified protein lysates (20-50 mg) were electrophoretically resolved on denaturing SDS-PAGE, transferred to nitrocellulose and probed with the following primary antibodies: anti-Her2 (C-18), -Her3 (C-17), -Raf-1, -cyclin D1, -Rb (C-15) (Santa Cruz Biotechnology), anti-hsp90, -hsp70 (Stressgen) anti-Trap-1 (MSK81), anti-b-actin, -tubulin (Sigma), ER, anti-PI3K (p85) (Upstate Biotechnologies).

Antiproliferative index. Growth assays were performed by seeding 10000 cells MCF-7 and MDA-MB-468) and 20000 cells (SKBr3) per well in 6-well dishes and incubating for 24 hrs before drug treatment. Drugs or vehicle were administered as outlined for each experiment, and cells were incubated for the time periods depicted and then the number quantified by a coulter counter.

Tissue Culture $IC_{50}$ Studies. Growth inhibition studies were performed using the sulforhodamine B assay described before. Experiments were performed with BT-474, MDA-MB-468, MCF-7, and TSU-Pr1. Stock cultures were grown in T-175's flask containing 30 mL of DME (HG, F-12, non-essential amino acids, and penicillin and streptomycin), with glutamine, and 10% FBS. TSU-Pr1 were grown in RPMI 1640 with glutamine and 10% FBS. Cells were dissociated with 0.05% trypsin and 0.02% EDTA in PBS without calcium and magnesium.

Experimental cultures were plated in microtiter plates (Nunc) in 100 uL of growth medium at densities of 1000 cells per well, except for BT-474 which were plated at densities of 3000 cells per well. One column of wells was left without cells to serve as the blank control. Cells were allowed to attach overnight (BT-474 were allowed to attach for 48 hours). The following day, an additional 100 uL of growth medium was added to each well. Stock drug or DMSO was dissolved in growth medium at twice the desired initial concentration. Drug or DMSO was serially diluted at a 1:1 ratio in the microtiter plate and added to duplicate wells. After 72 hours of growth, the cell number in treated versus control wells was estimated after treatment with 10% trichloroacetic acid and staining with 0.4% sulforhodamine B in 1% acetic acid. The $IC_{50}$ is calculated as the drug concentration that inhibits cell growth by 50% compared with control growth.

Her2 degradation. Total Protein Assays. Cells were grown to 60-70% confluence and exposed to drugs or DMSO vehicle for the indicated time periods. Lysates were prepared using 50 mM Tris pH 7.4, 2% SDS and 10% glycerol lysis buffer. Protein concentration was determined using the BCA kit (Pierce Chemical Co.), according to the manufacturers instructions. Clarified protein lysates (20-50 µg) were electrophoretically resolved on denaturing SDS-PAGE, transferred to nitrocellulose and probed with the anti-Her2 primary antibody (C-18) (Santa Cruz Biotechnology).

Binding studies. Solid phase competition assays. GM was immobilized on Affigel 10 resin (BioRad) as described[2]. The GM-beads were washed with TEN buffer (50 mM Tris.HCl pH 7.4, 1 mM EDTA, 1% NP-40) containing protease inhibitors and then blocked for 45 min at 4° C. with 0.5% BSA in TEN buffer. Hsp90 protein from Stressgen (SPP-770) was incubated with or without drugs for 17 min on ice. To each sample were added 20 µL GM-beads and the mixtures were rotated at 4° C. for 1 hr followed by 3 washes with 500 µL ice cold TEN each. The GM-beads bound protein was eluted from the solid phase by heating in 65 µL 1×SDS. Samples were portioned in a 20 µL aliquot for Hsp90 alpha analysis and a 40 µL aliquot for Hsp90 beta analysis, applied to a SDS/PAGE gel and visualized by immunoblotting with Hsp90 alpha (Stressgen # SPA-840) and Hsp90 beta (NeoMarkers#RB-118), respectively.

Compounds PU4-72 were tested for binding to Hsp90, degradation of Her2 total protein and for their antiproliferative effect. The results are summarized in Tables 1, 2, 3 and 4.

TABLE 1

Influence of the nature of the 9-N chain on activity

| | | $EC_{50}$ Hsp90 α | $EC_{50}$ Hsp90 β | $IC_{50}$ MCF-7 | $IC_{50}$ Her2/ MCF-7 | $IC_{50}$ BT-474 | $IC_{50}$ MDA-468 |
|---|---|---|---|---|---|---|---|
| PU13 | 4 | | | 70 | | | 75 |
| PU22 | 5 | | | 80 | | | 118 |
| PU43 | 6 | 6.6 | 10.8 | 47 | 50 | | 54 |
| PU3 | 7 | 15 | 13 | 50 | 55 | | 61 |
| PU21 | 8 | 22.5 | 11.8 | 62 | 50 | | 73 |
| PU41 | 9 | 16.6 | 20.4 | 98 | 100 | | 70 |
| PU9 | 10 | 28 | | 114 | 69 | | 85 |
| PU14 | 11 | 62.3 | 52.1 | 160 | >100 | | 130 |
| PU26 | 13 | 25.3 | 15.7 | 62 | 70 | | 71 |
| PU15 | 15 | 12 | 16.2 | 75 | 70 | | 70 |
| PU30 | 16 | 111.3 | 47.8 | 111 | 120 | | |
| PU16 | 17 | 17 | 32 | 46 | 60 | | 68 |
| PU4 | 18 | 120 | >100 | 70 | 50 | | |
| PU23 | 22 | 13.3 | 9.5 | 47 | 50 | | 55 |
| PU7 | 23 | 17.6 | 75 | 64 | 70 | | 80 |
| PU8 | 24 | 4 | 10.6 | 41 | 30 | | 73 |
| PU11 | 25 | | | 51 | | | 66 |
| PU24 | 26 | 2.6 | 1.5 | 24 | 20 | | 41 |
| PU25 | 36 | | | 82 | | | |
| PU44 | 37 | 4.1 | 12.4 | 65 | 85 | | 79 |
| PU29 | 38 | 1.4 | 1.7 | 39 | 45 | | 72 |
| PU20 | 41 | 4.4 | 3.4 | 92 | 70 | | 80 |

*all other compounds from FIG. 6B were either inactive or insoluble

TABLE 2

The influence of C-2 fluorination on activity

| | | $EC_{50}$ Hsp90 α | $EC_{50}$ Hsp90 β | $IC_{50}$ MCF-7 | $IC_{50}$ Her2/ MCF-7 | $IC_{50}$ BT-474 | $IC_{50}$ MDA-468 |
|---|---|---|---|---|---|---|---|
| PU43F | 47 | 4.1 | 5.3 | 25 | 30 | 30 | 25 |
| PU3F | 48 | 6 | 3.5 | 24 | 25 | 29 | 30 |
| PU21F | 49 | 22 | 8.9 | 36 | 35 | 43 | 19 |
| PU44F | 50 | 7.9 | 13.8 | 64 | 65 | 60 | 35 |
| PU26F | 51 | 22 | 15 | 44 | 40 | 45 | 28 |
| PU29F | 52 | 2 | 1.3 | 16 | 15 | | 16 |
| PU8F | 53 | 5 | 9.8 | 33 | 30 | 35 | 25 |
| PU47F | 54 | 10.7 | 9.9 | 45 | 50 | 46 | 33 |
| PU48F | 55 | 10 | 3.5 | 25 | 20 | 28 | 16 |
| PU49F | 56 | 15 | 10.4 | 37 | 45 | 33 | 45 |
| PU24F | 57 | 6.2 | 0.7 | 11 | 5 | 14 | 15 |
| PU16F | 58 | 30.7 | 9.2 | 41 | 40 | 31 | 21 |
| PU20F | 59 | 2.3 | 6.8 | 23 | 20 | 25 | 21 |

Addition of either CN, vinyl, iodine, methoxy, ethoxy, $NH_2$ at position 2 of the purine moiety decreased or abolished activity.

TABLE 3

The influence of introduction of an electron-donor group on the phenyl moiety

| | | $EC_{50}$ Hsp90 α | $EC_{50}$ Hsp90 β | $IC_{50}$ MCF-7 | $IC_{50}$ Her2/ MCF-7 | $IC_{50}$ BT-474 | $IC_{50}$ MDA-468 |
|---|---|---|---|---|---|---|---|
| PU3 | 7 | 15 | 13 | 50 | 55 | | 61 |
| PU3PhCl | 65 | 18.6 | 4.6 | 19 | 25 | 30 | 36 |
| PU3PhBr | 66 | 35.3 | 11.7 | 25 | 50 | 60 | INSOL |
| PU3PhBr2 | 67 | >100 | >100 | 30 | >100 | | 21 |

Assimilation of the best substituents resulted in the derivatives 71 and 72 (Table 4).

TABLE 4

| PU24FCl | 71 | 0.55 | 0.45 | 2 | 2 | 4.5 | 3 |
|---|---|---|---|---|---|---|---|
| PU29FCl | 72 | 0.65 | 0.52 | 5.4 | 3 | 4.5 | 4.5 |

EXAMPLE 9

Figure 17A:
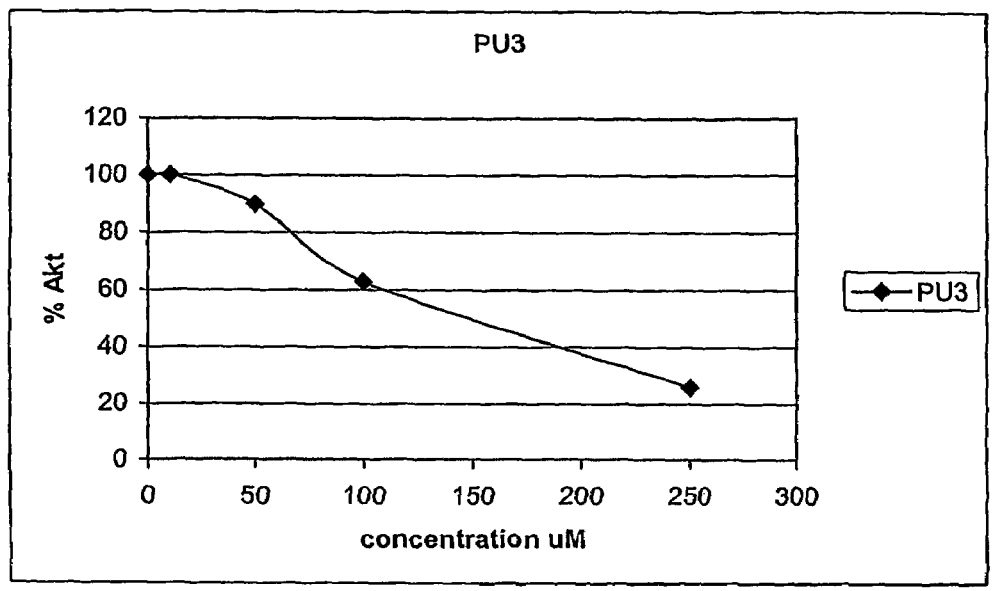
FIGS. 17A and B show degradation of Akt protein by PU3 and PU24FC1.
Figure 17B:
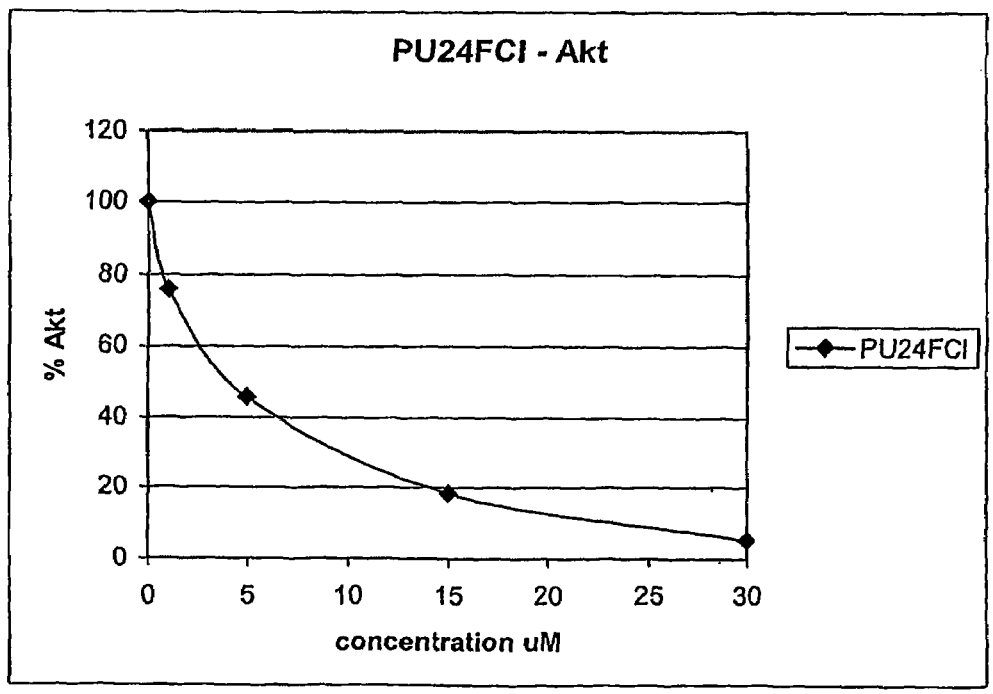

The ability of PU3 and PU24FCl to induce degradation of Akt protein. As shown in FIGS. 17A and B, the 30-fold difference in activity which was observed for Her2 degradation was also reflected in degradation of Akt. An approximately 30-fold difference was also seen in the Hsp90 binding affinity.

EXAMPLE 10

Figure 18A:
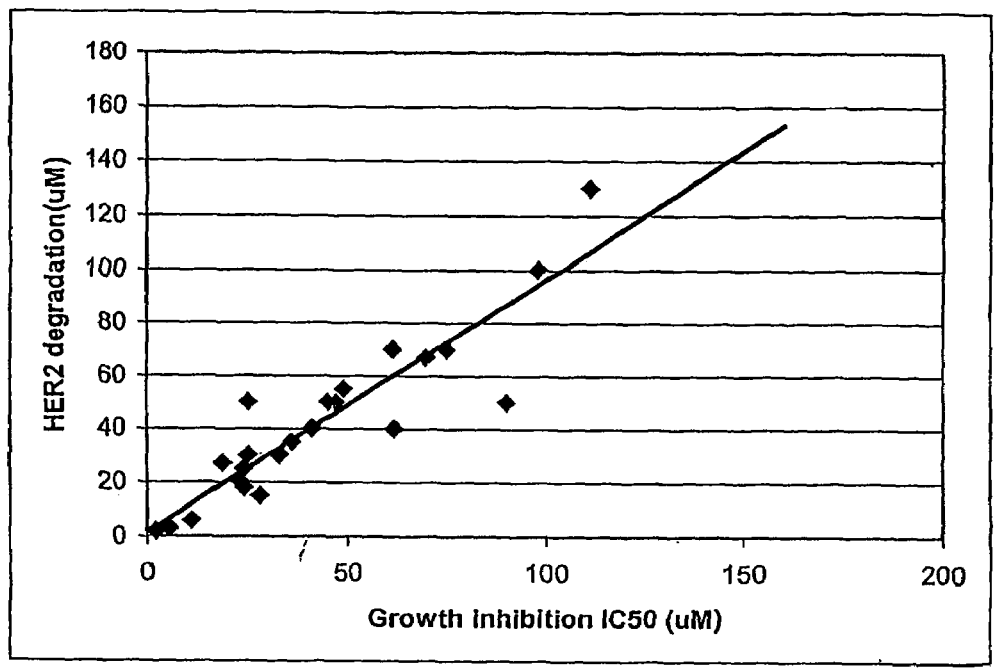
FIGS. 18 A and B show the correlation between growth arrest, Her2 total protein degradation and Hsp90 binding efficacy.
Figure 18B:
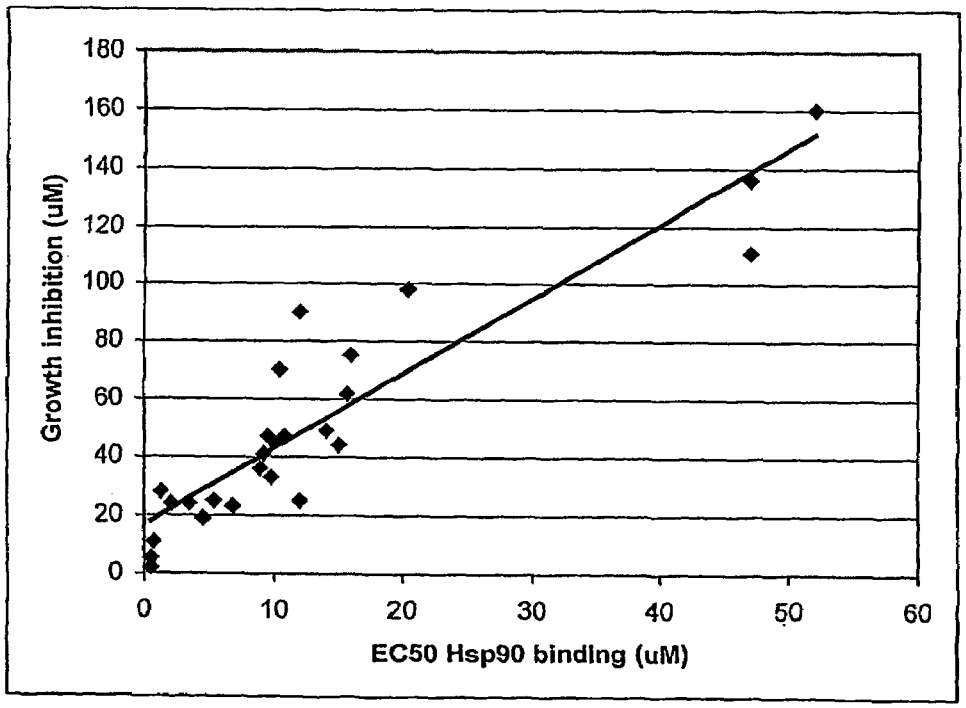

Data was analyzed to see if there was a correlation between concentrations of PU-series compounds effective for inducing Her2 degradation and the concentrations required for growth inhibition in the MCF-7 cell line, and between the Hsp90 binding constant and the concentrations required for growth inhibition. As shown in FIGS. 18A and B, the experimental results suggest a good correlation between growth arrest, Her2 total protein degradation and Hsp90 binding efficacy.

EXAMPLE 11

Cell culture. The human cancer cell lines MCF-7, SKBr3 and BT-474 were obtained from the American Type Culture Collection (Manassas, Va.) and maintained in 1:1 mixture of DME:F12 supplemented with 2 mM glutamine, 50 units/mL penicillin, 50 units/mL streptomycin and 5% (for MCF-7) or 10% (for SKBr3 and BT-474) heat inactivated fetal bovine serum (Gemini Bioproducts) and incubated at 37° C. in 5% $CO_2$.

Figure 19:
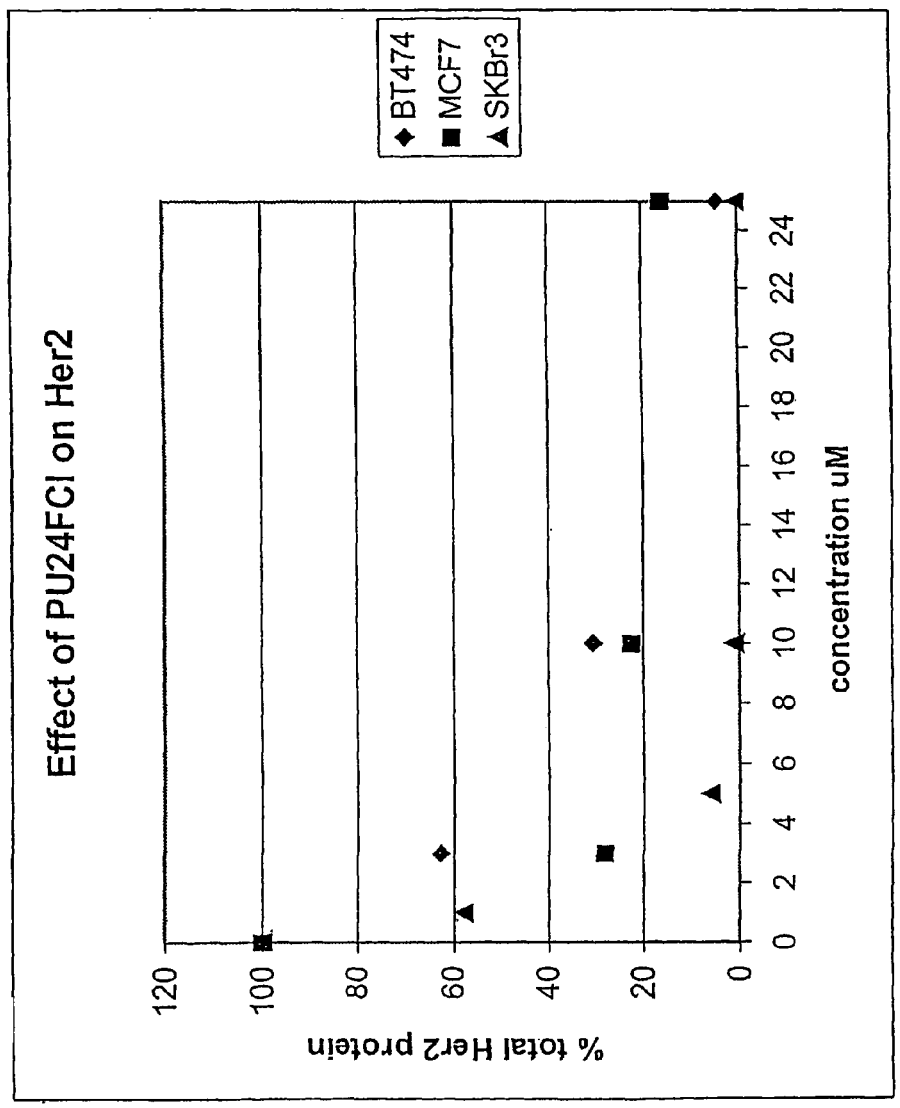
FIG. 19 shows Her2 degradation with PU24FC1.

Her2 degradation. Total Protein Assays. Cells were grown to 60-70% confluence and exposed to drugs or DMSO vehicle for the indicated time periods. Lysates were prepared using 50 mM Tris pH 7.4, 2% SDS and 10% glycerol lysis buffer. Protein concentration was determined using the BCA kit (Pierce Chemical Co.), according to the manufacturers instructions. Clarified protein lysates (20-50 μg) were electrophoretically resolved on denaturing SDS-PAGE, transferred to nitrocellulose and probed with the anti-Her2 primary antibody (C-18) (Santa Cruz Biotechnology). As shown in FIG. 19, PU24FCl induces efficient degradation of the oncogenic protein Her2 at low concentrations (IC50 of 1.7, 2, 4.5 uM for SKBr3, MCF-7 and BT-474 respectively).

What is claimed is:

1. A compound of the formula:

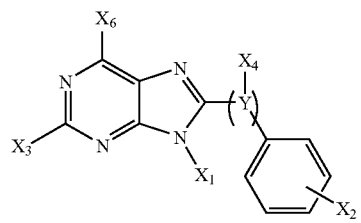

wherein Y is CH, O, N or O—CH,
X$_1$ is the substituent formed by removing the OH from an alcohol selected from the group consisting of

—OH        4

-continued

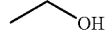  5

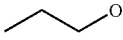  6

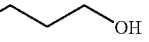  7

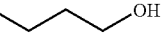  8

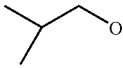  9

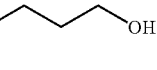  10

-continued

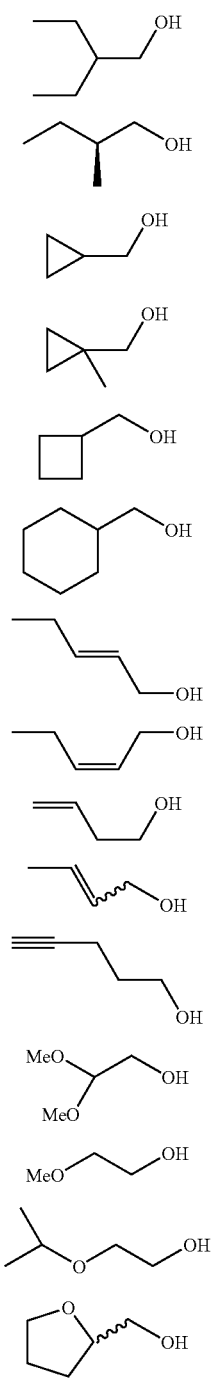

$X_2$ is from one to five non-hydrogen groups independently selected from the group consisting of halogen and methoxy, $X_3$ is halogen,
$X_4$ is absent when Y is O, or $X_4$ is hydrogen, halogen, alkyl, alkoxy, —SCH$_3$ or —SCH$_2$CH$_3$, and
$X_6$ is —NH$_2$, —OH, —O-Alkyl, or —CONH$_2$.

2. The compound according to claim 1, wherein $X_2$ is 1, 2, 3 trimethoxy.

3. The compound of claim 1, wherein $X_6$ is —NH$_2$.

4. The compound according to claim 3, wherein $X_2$ is 1, 2, 3 trimethoxy.

5. The compound of claim 1, having the structure wherein Me is methyl, and $X_7$ is hydrogen or halogen.

6. The compound of claim 1, having the structure wherein Me is methyl.

7. The compound of claim 1 having the structure wherein Me is methyl.

* * * * *

```
                        SEQUENCE LISTING

<160> NUMBER OF SEQ ID NOS: 4

<210> SEQ ID NO 1
    <211> LENGTH: 220
    <212> TYPE: PRT
    <213> ORGANISM: human

<400> SEQUENCE: 1

Ala Phe Gln Ala Glu Ile Ala Gln Leu Met Ser Leu Ile Ile Asn Thr
    1               5                   10                  15

Phe Tyr Ser Asn Lys Glu Ile Phe Leu Arg Glu Leu Ile Ser Asn Ser
                20                  25                  30

Ser Asp Ala Leu Asp Lys Ile Arg Tyr Glu Thr Leu Thr Asp Pro Ser
            35                  40                  45

Lys Leu Asp Ser Gly Lys Glu Leu His Ile Asn Leu Ile Pro Asn Lys
        50                  55                  60

Gln Asp Arg Thr Leu Thr Ile Val Asp Thr Gly Ile Gly Met Thr Lys
    65                  70                  75                  80

Ala Asp Leu Ile Asn Asn Leu Gly Thr Ile Ala Lys Ser Gly Thr Lys
                    85                  90                  95

Ala Phe Met Glu Ala Leu Gln Ala Gly Ala Asp Ile Ser Met Ile Gly
                100                 105                 110

Gln Phe Gly Val Gly Phe Tyr Ser Ala Tyr Leu Val Ala Glu Lys Val
            115                 120                 125

Thr Val Ile Thr Lys His Asn Asp Asp Glu Gln Tyr Ala Trp Glu Ser
        130                 135                 140

Ser Ala Gly Gly Ser Phe Thr Val Arg Thr Asp Thr Gly Glu Pro Met
    145                 150                 155                 160

Gly Arg Gly Thr Lys Val Ile Leu His Leu Lys Glu Asp Gln Thr Glu
                    165                 170                 175

Tyr Leu Glu Glu Arg Arg Ile Lys Glu Ile Val Lys Lys His Ser Gln
                180                 185                 190

Phe Ile Gly Tyr Pro Ile Thr Leu Phe Val Glu Lys Glu Arg Asp Lys
            195                 200                 205

Glu Val Ser Asp Asp Glu Ala Glu Lys Glu Asp
        210                 215                 220

<210> SEQ ID NO 2
    <211> LENGTH: 220
    <212> TYPE: PRT
    <213> ORGANISM: human

<400> SEQUENCE: 2
```

```
Glu Val Asn Arg Met Lys Leu Ile Ile Asn Ser Leu Tyr Lys Asn
1               5                   10                  15

Lys Glu Ile Phe Leu Arg Glu Leu Ile Ser Asn Ala Ser Asp Ala Leu
            20                  25                  30

Asp Lys Ile Arg Leu Ile Ser Leu Thr Asp Glu Asn Ala Leu Ser Gly
        35                  40                  45

Asn Glu Glu Leu Thr Val Lys Ile Lys Cys Asp Lys Glu Lys Asn Leu
    50                  55                  60

Leu His Val Thr Asp Thr Gly Val Gly Met Thr Arg Glu Glu Leu Val
65                  70                  75                  80

Lys Asn Leu Gly Thr Ile Ala Lys Ser Gly Thr Ser Glu Phe Leu Asn
                85                  90                  95

Lys Met Thr Glu Ala Gln Glu Asp Gly Gln Ser Thr Ser Glu Leu Ile
                100                 105                 110

Gly Gln Phe Gly Val Gly Phe Tyr Ser Ala Phe Leu Val Ala Asp Lys
            115                 120                 125

Val Ile Val Thr Ser Lys His Asn Asn Asp Thr Gln His Ile Trp Glu
    130                 135                 140

Ser Asp Ser Asn Glu Phe Ser Val Ile Ala Asp Pro Arg Gly Asn Thr
145                 150                 155                 160

Leu Gly Arg Gly Thr Thr Ile Thr Leu Val Leu Lys Glu Glu Ala Ser
                165                 170                 175

Asp Tyr Leu Glu Leu Asp Thr Ile Lys Asn Leu Val Lys Lys Tyr Ser
            180                 185                 190

Gln Phe Ile Asn Phe Pro Ile Tyr Val Trp Ser Ser Lys Thr Glu Thr
        195                 200                 205

Val Glu Glu Pro Met Glu Glu Glu Ala Ala Lys
    210                 215                 220

<210> SEQ ID NO 3
<211> LENGTH: 190
<212> TYPE: PRT
<213> ORGANISM: human

<400> SEQUENCE: 3

Ile Ala Gln Leu Met Ser Leu Ile Ile Asn Thr Phe Tyr Ser Asn Lys
1               5                   10                  15

Glu Ile Phe Leu Arg Glu Leu Ile Ser Asn Ala Ser Asp Ala Leu Asp
            20                  25                  30

Lys Ile Arg Tyr Glu Ser Leu Thr Asp Pro Ser Lys Leu Asp Ser Gly
        35                  40                  45

Lys Glu Leu Lys Ile Asp Ile Ile Pro Asn Pro Gln Glu Arg Thr Leu
    50                  55                  60

Thr Leu Val Asp Thr Gly Ile Gly Met Thr Lys Ala Asp Leu Ile Asn
65                  70                  75                  80

Asn Leu Gly Thr Ile Ala Lys Ser Gly Thr Lys Ala Phe Met Glu Ala
                85                  90                  95

Leu Gln Ala Gly Ala Asp Ile Ser Met Ile Gly Gln Phe Gly Val Gly
                100                 105                 110

Phe Tyr Ser Ala Tyr Leu Val Ala Glu Lys Val Val Ile Thr Lys
            115                 120                 125

His Asn Asp Asp Glu Gln Tyr Ala Trp Glu Ser Ser Ala Gly Gly Ser
    130                 135                 140

Phe Thr Val Arg Ala Asp His Gly Glu Pro Ile Gly Arg Gly Thr Lys
145                 150                 155                 160
```

```
Val Ile Leu His Leu Lys Glu Asp Gln Thr Glu Tyr Leu Glu Arg
                165                 170                 175

Arg Val Lys Glu Val Val Lys Lys His Ser Gln Phe Ile Gly
            180                 185                 190

<210> SEQ ID NO 4
<211> LENGTH: 190
<212> TYPE: PRT
<213> ORGANISM: human

<400> SEQUENCE: 4

Gln Ala Glu Thr Lys Lys Leu Leu Asp Ile Val Ala Arg Ser Leu Tyr
  1               5                  10                  15

Ser Glu Lys Glu Val Phe Ile Arg Glu Leu Ile Ser Asn Ala Ser Asp
             20                  25                  30

Ala Leu Glu Lys Leu Arg His Lys Leu Val Ser Asp Gly Gln Ala Leu
         35                  40                  45

Pro Glu Met Glu Ile His Leu Gln Thr Asn Ala Glu Lys Gly Thr Ile
 50                  55                  60

Thr Ile Gln Asp Thr Gly Ile Gly Met Thr Gln Glu Glu Leu Val Ser
 65                  70                  75                  80

Asn Leu Gly Thr Ile Ala Arg Ser Gly Ser Lys Ala Phe Leu Asp Ala
             85                  90                  95

Leu Gln Asn Gln Ala Glu Ala Ser Ser Lys Ile Ile Gly Gln Phe Gly
            100                 105                 110

Val Gly Phe Tyr Ser Ala Phe Met Val Ala Asp Arg Val Glu Val Tyr
            115                 120                 125

Ser Arg Ser Ala Ala Pro Gly Ser Leu Gly Tyr Gln Trp Leu Ser Asp
            130                 135                 140

Gly Ser Gly Val Phe Glu Ile Ala Glu Ala Ser Gly Val Arg Thr Gly
145                 150                 155                 160

Thr Lys Ile Ile Ile His Leu Lys Ser Asp Cys Lys Glu Phe Ser Ser
                165                 170                 175

Glu Ala Arg Val Arg Asp Val Val Thr Lys Tyr Ser Asn Phe
            180                 185                 190
```